United States Patent
Nojiri et al.

(10) Patent No.: US 11,397,160 B2
(45) Date of Patent: Jul. 26, 2022

(54) GAS SENSOR, GAS DETECTION DEVICE, GAS DETECTION METHOD AND DEVICE PROVIDED WITH GAS DETECTION DEVICE

(71) Applicant: SEMITEC Corporation, Tokyo (JP)

(72) Inventors: Toshiyuki Nojiri, Tokyo (JP); Dezhi Cheng, Tokyo (JP)

(73) Assignee: SEMITEC Corporation, Tokyo (JP)

(*) Notice: Subject to any disclaimer, the term of this patent is extended or adjusted under 35 U.S.C. 154(b) by 952 days.

(21) Appl. No.: 16/078,997

(22) PCT Filed: Feb. 15, 2017

(86) PCT No.: PCT/JP2017/005457
§ 371 (c)(1),
(2) Date: Aug. 22, 2018

(87) PCT Pub. No.: WO2017/145889
PCT Pub. Date: Aug. 31, 2017

(65) Prior Publication Data
US 2019/0049398 A1 Feb. 14, 2019

(30) Foreign Application Priority Data
Feb. 22, 2016 (JP) ................................ 2016-030929

(51) Int. Cl.
| | |
|---|---|
| *G01N 27/18* | (2006.01) |
| *G01N 25/48* | (2006.01) |
| *G01N 27/12* | (2006.01) |
| *G01N 33/00* | (2006.01) |

(52) U.S. Cl.
CPC ............ *G01N 27/18* (2013.01); *G01N 25/48* (2013.01); *G01N 25/4893* (2013.01); *G01N 27/12* (2013.01); *G01N 33/0036* (2013.01)

(58) Field of Classification Search
CPC .... G01N 27/18; G01N 25/4893; G01N 27/12; G01N 33/0036; G01N 25/48; G01N 27/14

(Continued)

(56) References Cited

U.S. PATENT DOCUMENTS 3,867,098 A * 2/1975 Gorkovenko .......... G01N 27/16
422/88
4,470,298 A * 9/1984 Jibelian .................. G01N 30/66
73/23.39

(Continued)

FOREIGN PATENT DOCUMENTS

| CN | 101607167 | 12/2009 |
|---|---|---|
| CN | 104407035 | 3/2015 |

(Continued)

OTHER PUBLICATIONS

"International Search Report (Form PCT/ISA/210)"of PCT/JP2017/005457, dated May 16, 2017, with English translation thereof, pp. 1-4.

(Continued)

*Primary Examiner* — Marrit Eyassu
(74) *Attorney, Agent, or Firm* — JCIPRNET

(57) ABSTRACT

Provided are a gas sensor, a gas detection device, a gas detection method and a device provided with the gas detection device, capable of improving gas detection performance. The gas detection device is provided with a gas sensor comprising a thermosensitive resistance element and a porous gas molecule adsorptive material thermally bonded to the thermosensitive resistance element that releases specified gas molecules due to heating and cooling, and a power supply control unit that heats and cools the thermosensitive resistance element by controlling the supply of power thereto. The gas detection method comprises a heating step for putting the porous gas molecule adsorptive material in a heated state and a detecting step for detecting a specific gas due to the temperature change in the thermosensitive resistance element by heating.

17 Claims, 18 Drawing Sheets

(58) Field of Classification Search
USPC .......................................................... 73/23.2
See application file for complete search history.

(56) References Cited

U.S. PATENT DOCUMENTS

| | | | | |
|---|---|---|---|---|
| 2002/0134234 | A1* | 9/2002 | Kalbassi | B01D 53/0462 96/111 |
| 2006/0240245 | A1* | 10/2006 | Ishida | G01N 27/12 428/312.6 |
| 2009/0114089 | A1* | 5/2009 | Liu | C01B 39/54 95/45 |
| 2013/0209315 | A1* | 8/2013 | Kimura | G01N 25/4826 422/88 |
| 2014/0113811 | A1* | 4/2014 | Stadie | B01J 20/28057 502/400 |
| 2014/0154811 | A1* | 6/2014 | Sjong | G01N 33/0016 436/72 |
| 2015/0153294 | A1* | 6/2015 | Watanabe | G01N 25/18 73/25.03 |
| 2015/0336864 | A1* | 11/2015 | Filipovic | B01D 53/70 502/407 |
| 2016/0084786 | A1* | 3/2016 | Suzuki | G01N 27/16 73/31.06 |

FOREIGN PATENT DOCUMENTS

| | | | | |
|---|---|---|---|---|
| CN | 105229451 | | 1/2016 | |
| CN | 105283756 | | 1/2016 | |
| EP | 2102630 | B1 * | 12/2014 | ............ B82Y 20/00 |
| JP | S5026593 | | 3/1975 | |
| JP | 02-085753 | | 3/1990 | |
| JP | H03220448 | | 9/1991 | |
| JP | H0829370 | | 2/1996 | |
| JP | 2003-262600 | | 9/2003 | |
| JP | 2004069465 | | 3/2004 | |
| JP | 2004069465 | A * | 3/2004 | |
| JP | 2007248220 | | 9/2007 | |
| JP | 3173006 | | 1/2012 | |
| JP | 2013242269 | | 12/2013 | |
| WO | 2014189119 | | 11/2014 | |
| WO | 2015087906 | | 6/2015 | |

OTHER PUBLICATIONS

"Office Action of China Counterpart Application", dated Aug. 31, 2020, with English translation thereof, p. 1-p. 21.
"Office Action of U.K. Counterpart Application", dated Jun. 28, 2021, p. 1-p. 4.
"Office Action of China Counterpart Application" with English translation thereof, dated Mar. 12, 2021, p. 1-p. 20.
"Office Action of China Counterpart Application" with English translation thereof, dated Aug. 18, 2021, p. 1-p. 21.
Office Action of U.K. Counterpart Application, dated Nov. 5, 2021, pp. 1-4.
"Office Action of China Counterpart Application" with English translation thereof, dated Nov. 3, 2021, p. 1-p. 22.

* cited by examiner

GAS SENSOR, GAS DETECTION DEVICE, GAS DETECTION METHOD AND DEVICE PROVIDED WITH GAS DETECTION DEVICE

CROSS-REFERENCE TO RELATED APPLICATION

This application is a 371 application of International PCT application serial no. PCT/JP2017/005457, filed on Feb. 15, 2017, which claims the priority benefit of Japan application no. 2016-030929, filed on Feb. 22, 2016. The entirety of each of the abovementioned patent applications is hereby incorporated by reference herein and made a part of this specification.

TECHNICAL FIELD

The present invention relates to a gas sensor, a gas detection device, a gas detection method, and a device provided with a gas detection device, capable of detecting gas molecules.

BACKGROUND ART

Conventionally, humidity sensors or gas sensors have been used as gas detection devices for detecting humidity or specific gases, for example, in household appliances, office automation (OA) equipment, food storage equipment, medical instruments, or the like.

In such gas detection devices, it is necessary to improve gas detection sensitivity at low temperature and gas selectivity to select detection target gases.

Incidentally, a humidity sensor including a moisture-sensitive resistance element in which a metal resistance wire is surrounded by a type A zeolite, for example, molecular sieve 5A is known (see Patent Literature 1 and Patent Literature 2).

Also, in order to enable a gas sensor to withstand a siloxane gas for a long time and to improve gas selectivity, a gas sensor in which a filter formed of zeolite, activated alumina, or the like is provided in a housing that accommodates a sensor body has been proposed (see Patent Literature 3).

Further, a humidity sensor in which a sensor element having a sensor chip is used or a humidity sensor in which a moisture-sensitive thin film formed by polymerizing a monomer is used has been proposed (see Patent Literature 4 and Patent Literature 5).

CITATION LIST

Patent Literature

[Patent Literature 1]
  Japanese Unexamined Patent Application No. H02-85753
[Patent Literature 2]
  Japanese Unexamined Patent Application No. H03-220448
[Patent Literature 3]
  Japanese Unexamined Patent Application No. 2013-242269
[Patent Literature 4]
  Japanese Utility Model Registration No. 3173006
[Patent Literature 5]
  Japanese Unexamined Patent Application No. 2003-262600

SUMMARY OF INVENTION

Technical Problem

However, a conventional humidity sensor is based on a principle of detecting humidity by detecting change in an electrical resistance value corresponding to a water vapor content in the atmosphere. Also, since the humidity sensors disclosed in Patent Literature 1 and Patent Literature 2 are adjusted to a high temperature by energizing a metal resistance wire so that the temperature is in a range of 300 to 500° C. there is a problem in that the energy for heating the metal resistance wire is large, power consumption is large, and a service life also is short.

Further, the gas sensor disclosed in Patent Literature 3 is provided with particular filters such as zeolite, activated alumina, activated carbon, or the like, and the humidity sensors disclosed in Patent Literature 4 and Patent Literature 5 have a problem in that gas detection sensitivity at low temperature is low.

The present invention has been made in view of the above-described problems, and it is an objective of the present invention to provide a gas sensor, a gas detection device, a gas detection method, and a device provided with a gas detection device, capable of improving gas detection performance.

Solution to Problem

A gas sensor according to a first aspect of the present invention includes a thermosensitive resistance element, and a porous gas molecule adsorption material thermally coupled to the thermosensitive resistance element and from which a specific gas molecule is desorbed by heating.

A gas sensor according to a second aspect of the present invention includes a thermosensitive resistance element, and a porous gas molecule adsorption material thermally coupled to the thermosensitive resistance element and in which a specific gas molecule is desorbed and adsorbed by heating and cooling.

The gas sensor according to a third aspect of the present invention is the gas sensor of the first or second aspect, including a compensating thermosensitive resistance element, and a material thermally coupled to the compensating thermosensitive resistance element and having adsorption properties different from those of the porous gas molecule adsorption material.

As the material having adsorption properties different from those of the porous gas molecule adsorption material, for example, a material such as a molecular sieve, alumina, or silica that has been heat treated and deactivated can be used. Also, while a molecular sieve 4A may be used as the porous gas molecule adsorption material, a molecular sieve 3A can also be used as the material having different adsorption properties. The material having different adsorption properties is not limited to a particular or specific material.

The gas sensor according to a fourth aspect of the present invention is the gas sensor of the third aspect, in which the compensating thermosensitive resistance element is accommodated in a sealed space.

The gas sensor according to a fifth aspect of the present invention is the gas sensor of any one of the first to fourth aspects, in which the thermosensitive resistance element is self-heatable when energized.

The gas sensor according to a sixth aspect of the present invention is the gas sensor of any one of the first to fifth aspects, in which a heating element which heats the porous gas molecule adsorption material is provided in addition to the thermosensitive resistance element.

The heating element may be a normal resistance heating element, an infrared lamp which heats indirectly, an infrared laser light, or the like. There is no limitation to any particular or specific one.

The gas sensor according to a seventh aspect of the present invention is the gas sensor of any one of the first to sixth aspects, in which the porous gas molecule adsorption material is a zeolite or a porous metal complex.

As zeolite, for example, a molecular sieve of a type A zeolite is suitably used. Porous metal complexes are new materials including coordination polymers or metal-organic framework obtained by utilizing metal complexes.

The gas sensor according to an eighth aspect of the present invention is the gas sensor of any one of the third to seventh aspects, in which the material having adsorption properties different from those of the porous gas molecule adsorption material is a material in which a porous gas molecule adsorption material is deactivated.

The gas sensor according to a ninth aspect of the present invention is the gas sensor of any one of the third to eighth aspects, in which the porous gas molecule adsorption material and the material having adsorption properties different from those of the porous gas molecule adsorption material have equivalent thermal properties.

Thermal properties mean, for example, a thermal conductivity, a specific heat capacity, or the like.

A gas detection device according to a tenth aspect of the present invention includes a gas sensor according to claim 1 or 3, and a supply power control unit which controls supply of power to the thermosensitive resistance element and heats the thermosensitive resistance element.

A gas detection device according to an eleventh aspect of the present invention includes a gas sensor according to claim 2 or 3, and a supply power control unit which controls supply of power to the thermosensitive resistance element, and heats and cools the thermosensitive resistance element.

The gas detection device according to a twelfth aspect of the present invention is the gas sensor of the tenth or eleventh aspect, in which the gas sensor is connected by a bridge circuit and a gas is detected by a differential output thereof.

The gas detection device according to a thirteenth aspect of the present invention is the gas sensor of the twelfth aspect, including an alternating current (AC) amplifier to which the differential output is connected.

A gas detection method according to a fourteenth aspect of the present invention, includes a thermosensitive resistance element, and a porous gas molecule adsorption material thermally coupled to the thermosensitive resistance element and from which a specific gas molecule is desorbed by heating, wherein the method includes a heating step of bringing the porous gas molecule adsorption material into a heated state; and a detection step of detecting a specific gas using a temperature change of the thermosensitive resistance element due to heating.

A gas detection method according to a fifteenth aspect of the present invention, includes a thermosensitive resistance element, and a porous gas molecule adsorption material thermally coupled to the thermosensitive resistance element and in which a specific gas molecule is desorbed and adsorbed by heating and cooling, wherein the method includes a heating step of bringing the porous gas molecule adsorption material into a heated state, a cooling step of bringing the porous gas molecule adsorption material into a cooled state at a temperature lower than that in the heating step, and a detection step of detecting a specific gas using a temperature change of the thermosensitive resistance element due to heating and the cooling.

The cooled state may be a state in which a temperature is lower than that in the heated state, and includes, for example, a case of having lowered a heating temperature by lowering an applied voltage and a case of setting the applied voltage to 0 V (stop).

The gas detection method according to a sixteenth aspect of the present invention is the gas detection method of the fifteenth aspect, in which the heating step and the cooling step are performed by being repeated at regular intervals.

A device provided with a gas detection device according to a seventeenth aspect of the present invention includes a gas detection device of any one of the tenth to thirteenth aspects.

A device in which the gas detection device is provided can be applied to various devices for detecting gas molecules and humidity in household appliances, office automation (OA) equipment, food storage equipment, medical instruments, transportation equipment such as automobiles, or the like. The device to which it is applied is not particularly limited.

Effects of Invention

According to the present invention, it is possible to provide a gas detection device, a gas detection method, and a device provided with a gas detection device, capable of improving gas detection performance.

BRIEF DESCRIPTION OF DRAWINGS

FIG. 1A and FIG. 1B illustrates a gas sensor according to a first embodiment of the present invention, in which FIG. 1A is a cross-sectional view and FIG. 1B is a cross-sectional view taken along line X-X of FIG. 1A.

FIG. 18A and FIG. 18B illustrates a gas sensor according to a fourth embodiment of the present invention, in which FIG. 18A is a cross-sectional view and FIG. 18B is a cross-sectional view of a thermosensitive resistance element corresponding to FIG. 1B.

FIG. 29A is a connection diagram illustrating the same (Example 3), in which FIG. 29A is a connection diagram and FIG. 29B is a cross-sectional view of a thermosensitive resistance element corresponding to FIG. 1B.

DESCRIPTION OF EMBODIMENTS

Figure 1A:
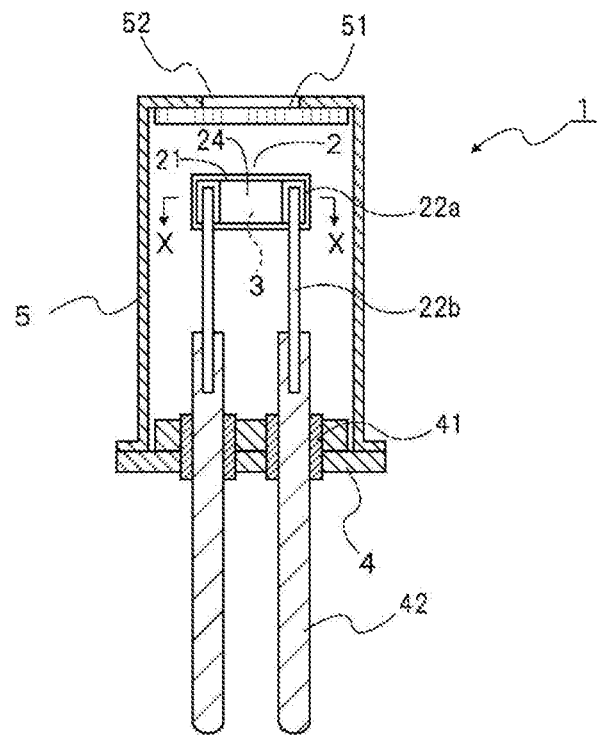
Figure 1B:
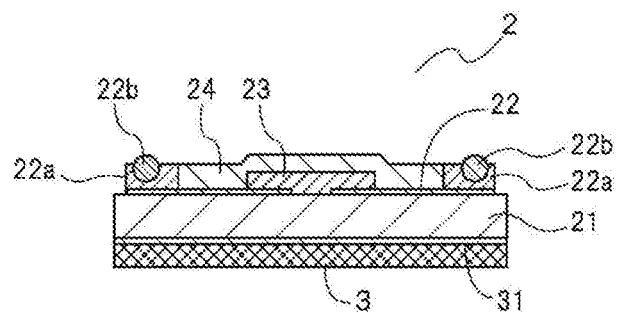
Figure 2:
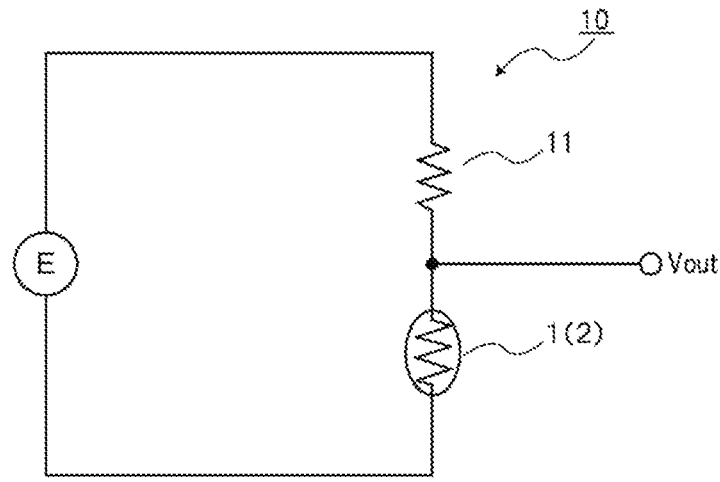
FIG. 2 is a connection diagram for characteristics detection of a gas detection device.
Figure 3:
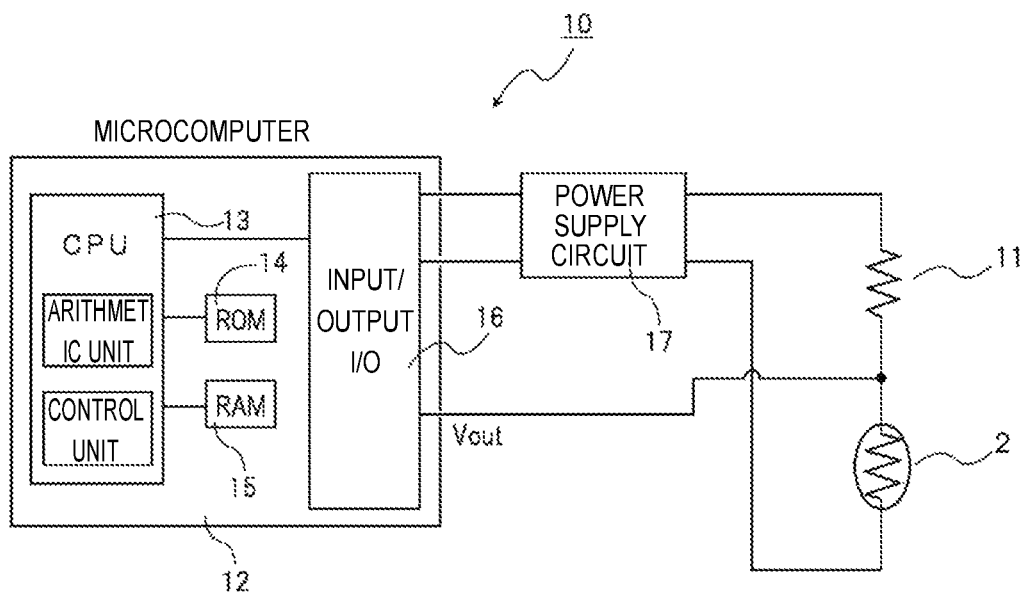
FIG. 3 is a block configuration diagram illustrating the gas detection device.
Figure 4:
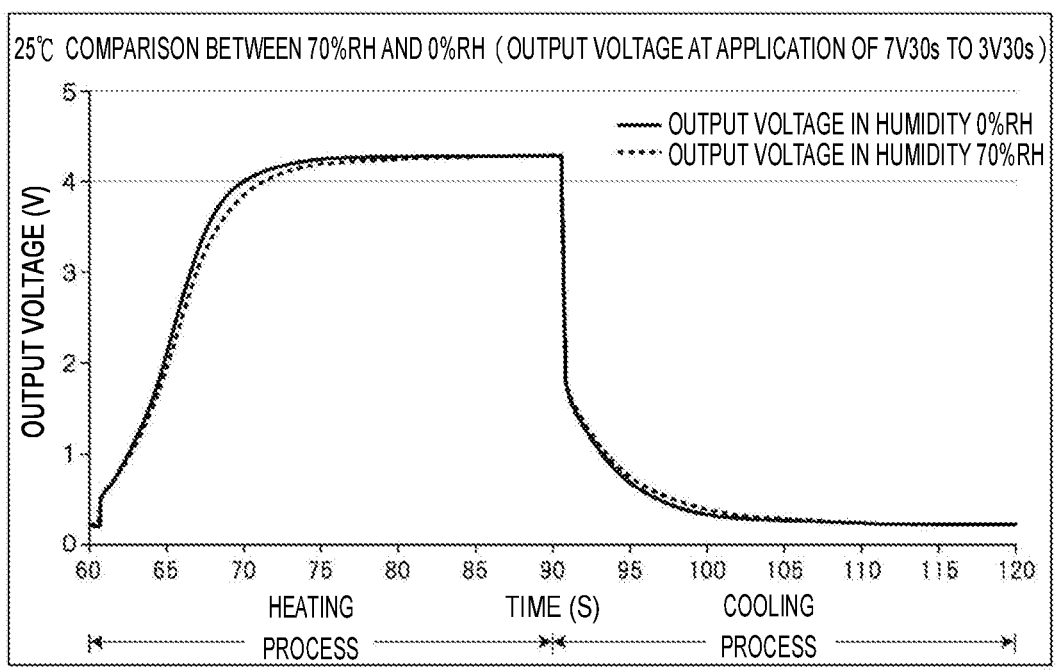
FIG. 4 is a graph showing a change in output voltage.
Figure 5:
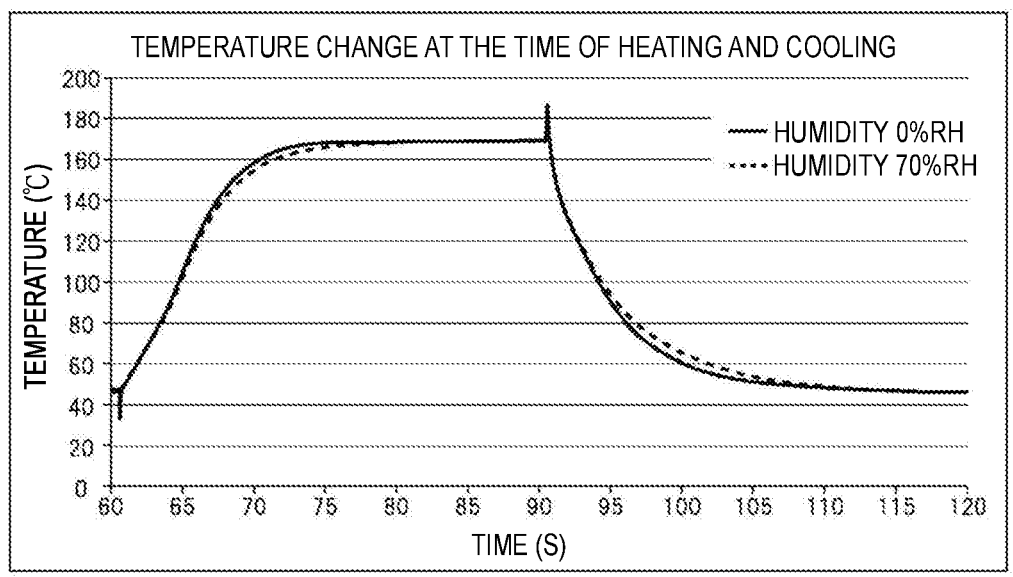
FIG. 5 is a graph showing a change in temperature.

Hereinafter, a gas sensor, a gas detection device, and a gas detection method according to a first embodiment of the present invention will be described with reference to FIGS. 1A to 5. FIG. 1A and FIG. 1B are cross-sectional views illustrating a gas sensor, FIG. 2 is a connection diagram for characteristics detection of a gas detection device, and FIG. 3 is a block configuration diagram illustrating the gas detection device. Further, FIGS. 4 and 5 are graphs showing a change in output voltage and a change in temperature of a thermosensitive resistance element.

As illustrated in FIG. 1A and FIG. 1B, a gas sensor 1 includes a thermosensitive resistance element 2, a gas molecule adsorption material 3, a base member 4, and an exterior case 5. In the present embodiment, the gas sensor 1 is a humidity sensor that detects water vapor gas (water molecules) in the atmosphere. Further, in each of the drawings, a scale of each member will be appropriately changed so that a size of each member is recognizable.

The thermosensitive resistance element 2 is a thin film thermistor and is a detecting thermosensitive resistance element. The thermosensitive resistance element 2 includes a substrate 21, a conductive layer 22 formed on the substrate 21, a thin film element layer 23, and a protective insulating layer 24.

The substrate 21 has a substantially rectangular shape and is formed using an insulating material including a ceramic such as alumina, aluminum nitride, or zirconia, and a semiconductor material such as silicon or germanium. On one surface of the substrate 21, an insulating thin film is formed using a sputtering method.

The conductive layer 22 constitutes an interconnection pattern, and is formed on the substrate 21. The conductive layer 22 is formed of a metal thin film using a sputtering method, and noble metals such as platinum (Pt), gold (Au), silver (Ag), and palladium (Pd), and alloys of these noble metals such as, for example, Ag—Pd alloy, are applied as a metal material thereof.

The thin film element layer 23 is a thermistor composition and is formed of an oxide semiconductor having a negative temperature coefficient. The thin film element layer 23 is formed on the conductive layer 22 using a sputtering method and is electrically connected to the conductive layer 22. Further, an electrode portion 22a electrically connected to the conductive layer 22 is formed at opposite end portions of the substrate 21.

The thin film element layer 23 is composed of two or more elements selected from transition metal elements, such as, for example, manganese (Mn), nickel (Ni), cobalt (Co), and iron (Fe). The protective insulating layer 24 is formed to cover the thin film element layer 23 and the conductive layer 22. A lead wire 22b is connected to the electrode portion 22a by soldering or the like.

Further, the thermosensitive resistance element is not limited to a thin film thermistor, and may be constituted by a thin film platinum resistance element. Also, a thermistor element constituted by a metal wire such as a platinum wire and a wire of an alloy thereof, or a semiconductor such as a metal oxide, a silicide, and a nitride may also be used. Further, the thermosensitive resistance element may be constituted by a thermocouple element such as a thermocouple or a thermopile in which a plurality of thermocouples is connected in series, and is not limited to a particular or specific one.

The gas molecule adsorption material 3 is thermally coupled to and provided for the thermosensitive resistance element 2 configured as above. Specifically, the gas molecule adsorption material 3 is held on the other surface side (back surface side) of the substrate 21 with an adhesive layer 31 such as a silicone adhesive having heat resistance of about 200° C. interposed therebetween. Therefore, the thermosensitive resistance element 2 and the gas molecule adsorption material 3 are thermally coupled with the substrate 21 interposed therebetween. That is, there is a configuration such that heat is bilaterally conducted between the thermosensitive resistance element 2 and the gas molecule adsorption material 3. Further, an inorganic or organic adhesive is appropriately used for the adhesive layer 31.

The gas molecule adsorption material 3 is a porous adsorption material and, for example, a molecular sieve 3A (pore diameter 0.3 nm) of a type A zeolite may be used.

The gas molecule adsorption material 3 is formed, for example, by finely pulverizing a molecular sieve 3A using a vibration mill, placing the finely pulverized powder substances in an electric furnace, and then heat treating the powder substances at about 650° C. for 1 hour to remove adsorbed gas molecules. The gas molecule adsorption material 3 of these powder substances are uniformly applied onto the adhesive layer 31. In this case, it is preferable to apply the gas molecule adsorption material 3 of the powder substances by electrostatic powder coating.

Since the gas molecule adsorption material 3 is applied to the adhesive layer 31, the gas molecule adsorption material 3 is not subjected to a heat treatment at high temperature at the time of the application. Therefore, although when the lead wire 22b is connected by soldering or the like, the solder is melted when heated at a high temperature of 200° C. or more, since such a heat treatment at high temperature is not performed at the time of the application, melting of the solder can be avoided.

Further, in a case in which the gas molecule adsorption material 3 is directly heat treated and applied to the substrate 21 without providing the adhesive layer 31, a slurry-like gas molecule adsorption material 3 may be formed on the back surface side of the substrate 21 in a process before the soldering of the lead wire 22b or the like.

Further, a molecular sieve 4A, 5A, or 13X, a high silica type zeolite, a silver zeolite substituted with metal ions, or the like, or a porous metal complex can be used for the gas molecule adsorption material 3 according to a detection target gas.

The base member 4 is a metal member formed in a substantially disc shape, and a conductive terminal portion 42 is inserted therethrough with an insulating member 41 interposed therebetween. The lead wire 22b led out from the thermosensitive resistance element 2 is electrically connected to the conductive terminal portion 42 by welding, soldering, or the like. The insulating member 41 is formed of an insulating material such as glass or a resin.

When the base member 4 is formed of an insulating material, the insulating member 41 may be unnecessary. Further, the conductive terminal portion 42 may be formed by a printed wiring board or the like.

The exterior case 5 is a metal member formed in a substantially cylindrical shape and having high thermal conductivity, and in which one end side is open and a circular opening 52 provided with a vent 51 is formed in the other end side. The exterior case 5 with one end side thereof attached to the base member 4 has a function of covering and protecting the thermosensitive resistance element 2.

The vent 51 is formed of a member having air permeability capable of reducing an influence of outside airflow and allowing gases to flow in and out, and the vent 51 is preferably formed of a material such as a wire mesh, a non-woven cloth, a porous sponge, or the like. The vent 51 is provided by being press-fitted or adhered to an inner circumferential side of the exterior case 5. Further, the vent 51 is not limited to being provided in the exterior case 5. The vent 51 may be provided in the base member 4, or a gap may be formed between the exterior case 5 and the base member 4 so that the vent 51 may be provided therein.

The exterior case 5 can be formed of a ceramic, a resin material, or the like. In this case, metal plating or the like may be applied to the exterior case 5 so that an inner wall surface thereof has a function of reflecting infrared light.

As illustrated in FIG. 2, a gas detection device 10 is configured by connecting a power supply (voltage source) E to the gas sensor 1. Specifically, a resistor 11 and the gas sensor 1 (thermosensitive resistance element 2) are connected in series to the power supply E, an output terminal is connected between the resistor 11 and the thermosensitive resistance element 2, and a voltage at both ends of the resistor 11 is detected as an output voltage Vout. The resistor 11 is a resistor for voltage detection and overcurrent protection.

As illustrated in FIG. 3, in the present embodiment, the gas detection device 10 is configured such that overall control is executed by a microcomputer 12 (hereinafter referred to as "microcomputer") serving as a control means. The microcomputer 12 is schematically configured with a central processing unit (CPU) 13 having an arithmetic unit and a control unit, a read-only memory (ROM) 14 and a random access memory (RAM) 15 serving as storage means, and input/output control means 16. Also, a power supply circuit 17 is connected to the input/output control means 16. In addition, the circuit illustrated in FIG. 2 is connected to the power supply circuit 17.

The power supply circuit 17 includes the power supply E and has a function of controlling supply of power to the thermosensitive resistance element 2 by varying a voltage of the power supply E. Specifically, supply of power by the power supply E in the power supply circuit 17 is controlled by a program stored in the storage means of the microcomputer 12. Further, the output voltage Vout is input to the microcomputer 12, arithmetically processed, and then output as a detection output.

Further, in the present embodiment, the control of supply of power of the power supply E is executed by, for example, means configured with the microcomputer 12 and the power supply circuit 17, that is, by a supply power control unit. The supply power control unit may have a function of controlling the supply of power of the power supply E, and is not limited to a particular or specific member or portion.

Next, an operation of the gas detection device 10 will be described with reference to both FIGS. 4 and 5. In the present embodiment, a case in which relative humidity RH is detected by converting from absolute humidity in atmospheric air is described.

As representatively illustrated in FIG. 3, when the gas detection device 10 is driven, a constant voltage of 7 V from the power supply E of the power supply circuit 17 is applied to the thermosensitive resistance element 2 for 30 seconds according to an output signal from the microcomputer 12. This state is a state in which the supply of power is controlled so that the thermosensitive resistance element 2 is heated. Next, a constant voltage of 3 V from the power supply E is applied to the thermosensitive resistance element 2 for 30 seconds. This state is a state in which the supply of power is controlled so that the thermosensitive resistance element 2 is cooled. That is, the thermosensitive resistance element 2 is controlled such that it transitions from a heating process to a cooling process. The thermosensitive resistance element 2 is self-heatable when energized. Further, an applied voltage in the heating process and the cooling process can be appropriately selected, and for example, the applied voltage in the cooling process may be 0 V, and a cooled state need only have a temperature lower than a heating temperature in a heated state.

On the other hand, the porous gas molecule adsorption material 3 is a molecular sieve 3A (pore diameter 0.3 nm) of a type A zeolite. This gas molecule adsorption material 3 causes a molecular sieve effect and adsorbs only molecules whose diameter is smaller than the pore diameter. Therefore, although hydrogen ($H_2$), helium (He), water vapor (water molecules) ($H_2O$) and ammonia ($NH_3$) in the atmosphere are adsorbed, amounts of each thereof other than water vapor ($H_2O$) are extremely minute, and thus an effect on the adsorption reaction is little. Therefore, water vapor ($H_2O$) can be selectively adsorbed, and selectivity of this detection target gas is enhanced.

In addition, the gas molecule adsorption material 3 has characteristics of causing an exothermic reaction when molecules are adsorbed and causing an endothermic reaction when molecules are desorbed. Therefore, the gas molecule adsorption material 3 acts such that heat is generated when water vapor ($H_2O$) is adsorbed and heat is adsorbed when water vapor ($H_2O$) is desorbed. That is, heat is adsorbed when water vapor ($H_2O$) is desorbed by heating the gas molecule adsorption material 3, and heat is generated when the gas molecule adsorption material 3 is cooled and water vapor ($H_2O$) is adsorbed.

A result of a change in an output voltage Vout in the supply power control as described above is shown in FIG. 4. In FIG. 4, a horizontal axis represents time (seconds) and a vertical axis represents an output voltage (V). Further, a solid line indicates a change in the output voltage Vout when the humidity is 0% RH, and a broken line indicates a change in the output voltage Vout when the humidity is 70% RH.

Further, FIG. 5 shows a change in temperature of the thermosensitive resistance element 2, in which a horizontal axis represents time (seconds) and a vertical axis represents a temperature (° C.). In addition, a solid line indicates a change in temperature when the humidity is 0% RH, and a broken line indicates a change in temperature when the humidity is 70% RH.

As illustrated in FIG. 4, in the cases of a humidity of 0% RH and a humidity of 70% RH, although a voltage difference is generated in the output voltage Vout in a first half of the heating process and the cooling process, the output voltage Vout stabilizes at about 4.3 V after heating is started in the heating process and, the output voltage Vout stabilizes at about 0.2 V after cooling is started in the cooling process.

Also, as shown in FIG. 5, similarly, a temperature difference is generated in the first half of the heating process and the cooling process. In the heating process, since water vapor ($H_2O$) is desorbed to cause an endothermic reaction in the gas molecule adsorption material 3, a temperature of the thermosensitive resistance element 2 at the humidity of 70% RH is lower than that at the humidity of 0% RH. In the cooling process, since water vapor ($H_2O$) is adsorbed to cause an exothermic reaction, the temperature of the thermosensitive resistance element 2 at the humidity of 70% RH is higher than that at the humidity of 0% RH.

Further, in the heating process, the temperature stabilizes at about 170° C. after heating is started, and in the cooling process, the temperature stabilizes at about 55° C. after cooling is started.

Therefore, a temperature change due to desorption and adsorption of water vapor gas (water molecules) from/to the gas molecule adsorption material 3 can be perceived in a cycle of heating process and cooling process over 30 seconds. Further, the heating process and the cooling process may be repeated over a plurality of cycles.

The gas detection device 10 detects humidity in the atmosphere schematically as follows. Patterns of an output voltage Vout change and/or a temperature change when the humidity is 0% RH as shown in FIGS. 4 and 5 are stored in the storage means of the microcomputer 12. This pattern serve as a reference.

When detecting a humidity of, for example 70% RH, in the atmosphere, water vapor ($H_2O$) flows in and out via the vent 51 due to heating and cooling processes and is desorbed from and adsorbed to the gas molecule adsorption material 3, and thereby patterns of the output voltage Vout change and/or the temperature change shown in FIGS. 4 and 5 can be obtained. The microcomputer 12 performs an operation of comparing these patterns with the reference pattern for a humidity of 0% RH stored in advance in the storage means. Next, the microcomputer 12 calculates and outputs the humidity of 70% RH according to a difference in the output voltage Vout change and/or a temperature change.

In the present embodiment as described above, a heating process (heating step) of heating the gas molecule adsorption material 3 and a cooling process (cooling step) of cooling the gas molecule adsorption material 3 at a temperature lower than that in the heating process are included, and a method of detecting a concentration of a specific gas by comparing a temperature change (voltage change) of the thermosensitive resistance element 2, specifically, by comparing a temperature change pattern of the detection target gas with the reference temperature change pattern is employed.

Further, in the above-described method of detecting a concentration of a gas, a concentration of the gas may be detected from a temperature change in both the heating process and the cooling process, in other words, from a difference in the output voltage Vout change and/or the temperature change, and a concentration of a gas may be detected from a temperature change in at least one of the heating process and the cooling process, in other words, from a difference in the output voltage Vout change and/or the temperature change.

Figure 6:
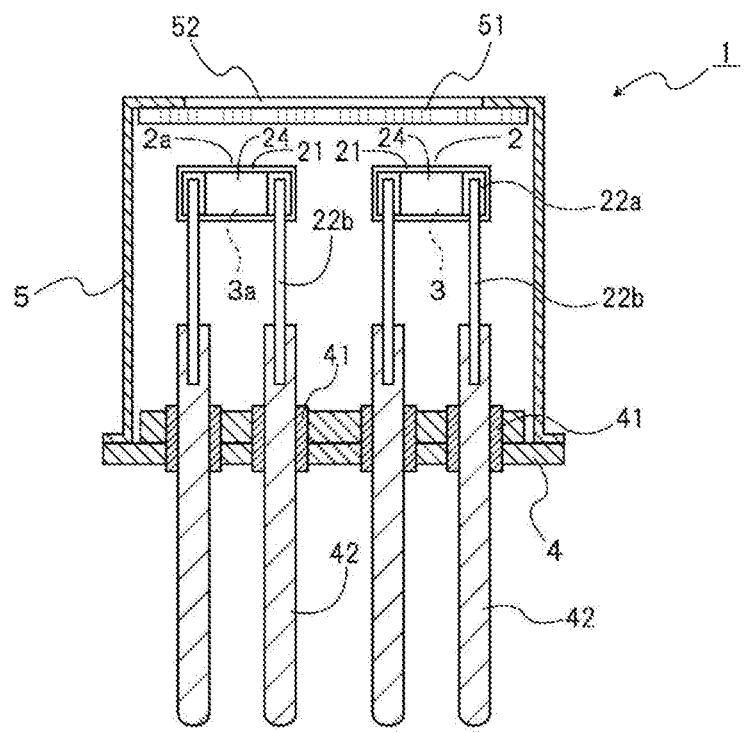
FIG. 6 is a cross-sectional view illustrating a gas sensor according to a second embodiment of the present invention.
Figure 7:
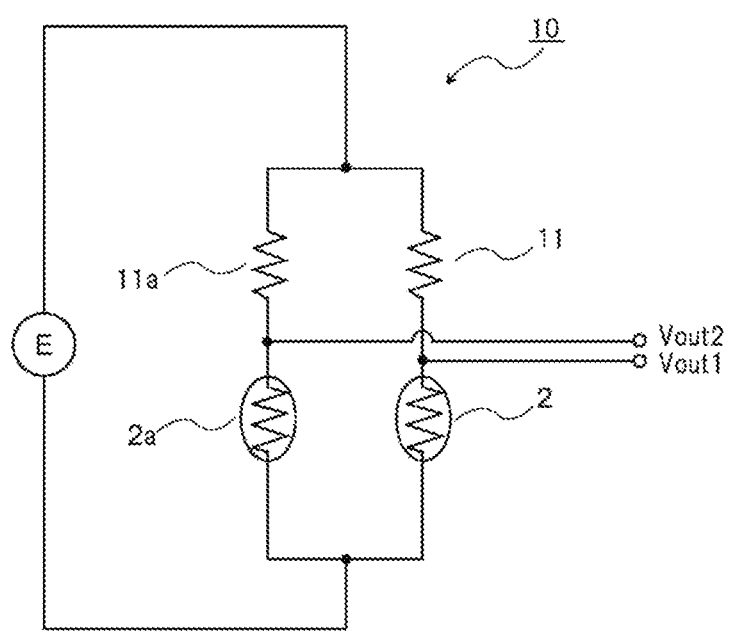
FIG. 7 is a connection diagram for detecting characteristics of a gas detection device.
Figure 8:
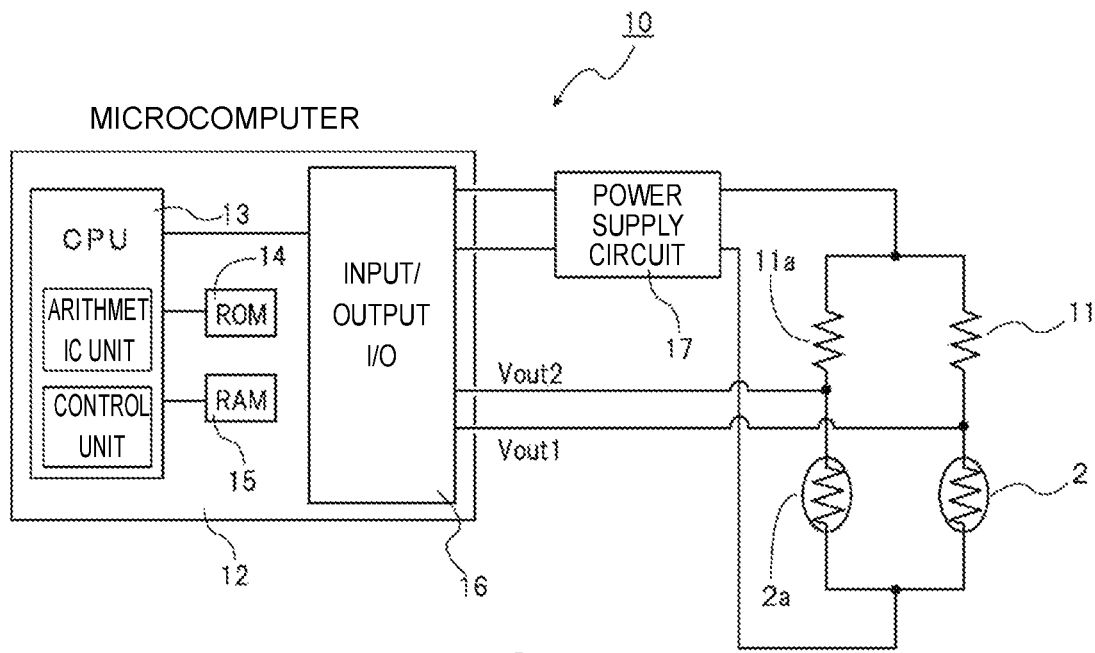
FIG. 8 is a block configuration diagram illustrating the gas detection device.
Figure 9:
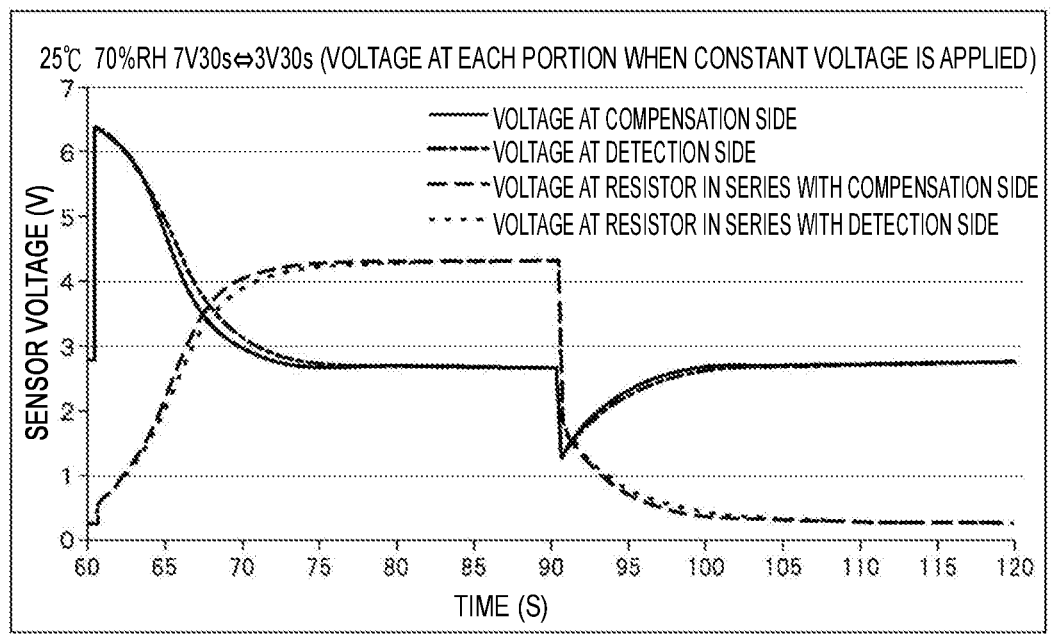
FIG. 9 is a graph showing a change in output voltage.
Figure 10:
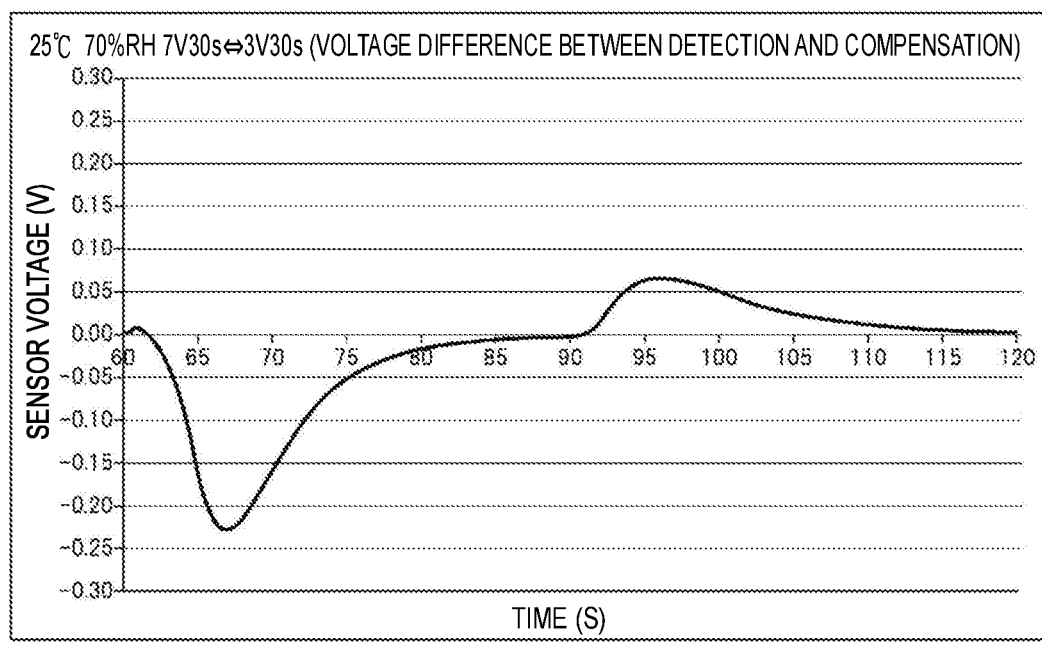
FIG. 10 is a graph showing a voltage difference of the output voltage.
Figure 11:
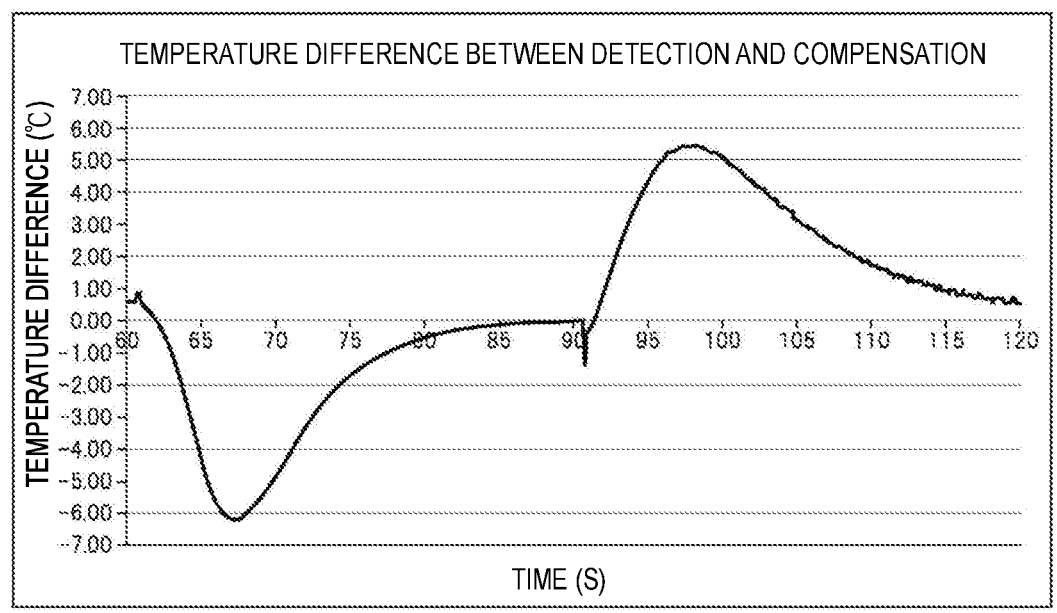
FIG. 11 is a graph showing a temperature difference.
Figure 12:
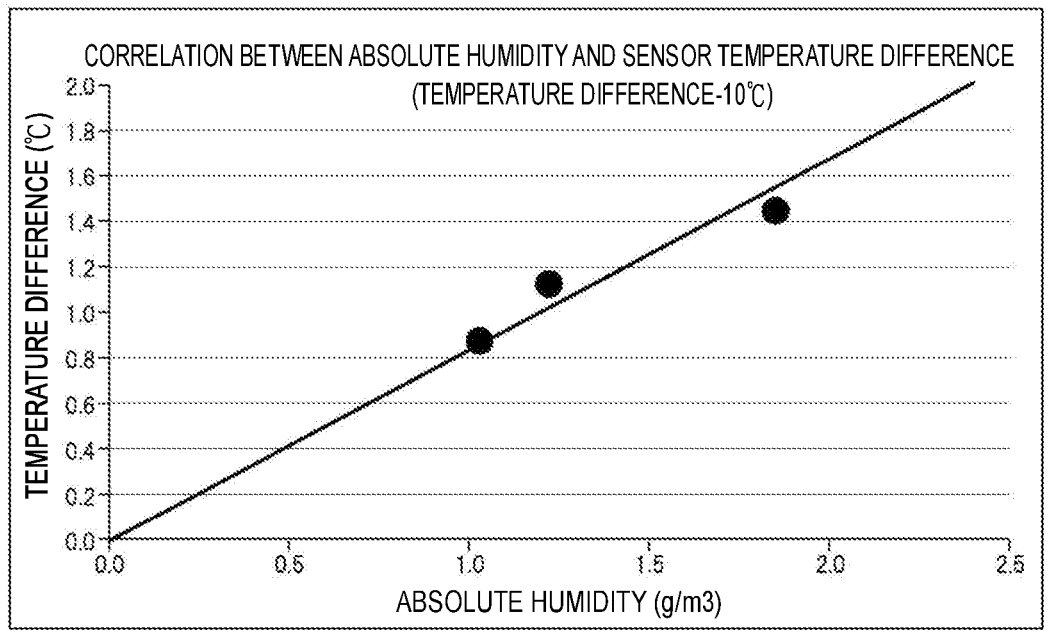
FIG. 12 is a graph showing a correlation between absolute humidity and a temperature difference in a low temperature environment.
Figure 13:
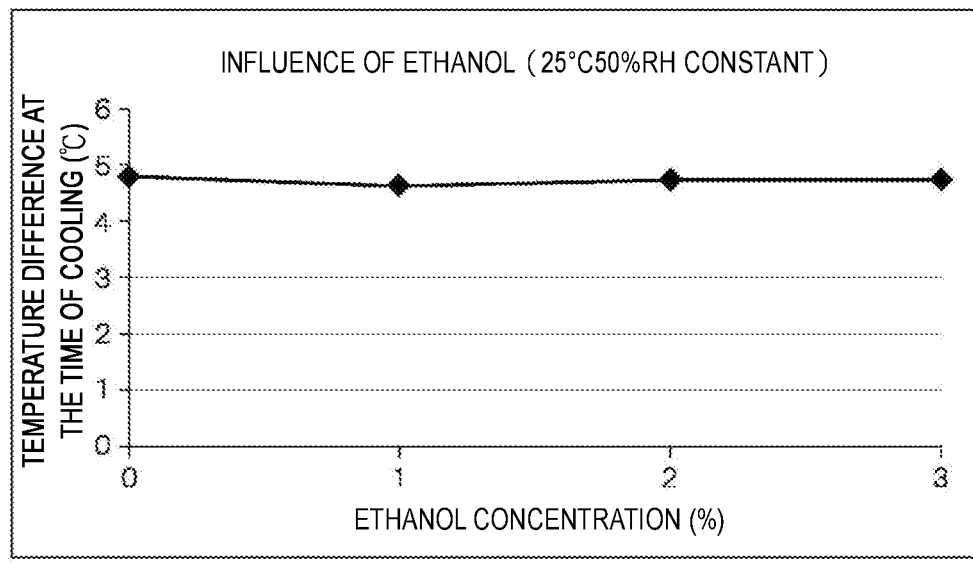
FIG. 13 is a graph showing a change in characteristics with respect to ethanol ($C_2H_6O$).

Next, a second embodiment of the present invention will be described with reference to FIGS. 6 to 13. FIG. 6 is a cross-sectional view illustrating a gas sensor, FIG. 7 is a connection diagram for detecting characteristics of a gas detection device, and FIG. 8 is a block configuration diagram illustrating the gas detection device. FIG. 9 shows a change in output voltage, and FIGS. 10 and 11 are graphs showing a voltage difference and a temperature difference between a detecting thermosensitive resistance element and a compensating thermosensitive resistance element. FIG. 12 is a graph showing a correlation between absolute humidity and a temperature difference in a low temperature environment. FIG. 13 is a graph showing a change in characteristics with respect to ethanol ($C_2H_6O$). Portions the same as or corresponding to those in the first embodiment are denoted by the same reference signs, and duplicate description thereof will be omitted.

As illustrated in FIG. 6, a gas sensor 1 of the present embodiment is a humidity sensor that detects water vapor gas (water molecules) in the atmosphere, and includes a pair of thermosensitive resistance elements. That is, a detecting thermosensitive resistance element 2 and a compensating thermosensitive resistance element 2a are provided to be covered with an exterior case 5. Gas molecule adsorption materials 3 and 3a are applied to a back surface side of a substrate 21 of the detecting thermosensitive resistance element 2 and the compensating thermosensitive resistance element 2a. The detecting thermosensitive resistance element 2 and the compensating thermosensitive resistance element 2a basically have the same configuration, but a configuration of the gas molecule adsorption material 3a provided in the compensating thermosensitive resistance element 2a is different. The gas molecule adsorption material 3a is a material having adsorption properties different from those of the porous gas molecule adsorption material 3, and a deactivated molecular sieve 3A of a type A zeolite is used.

This deactivated molecular sieve 3A is prepared by further heat treating powder substances formed by removing adsorbed gas molecules as in the first embodiment at a temperature of about 850° C. for several hours to destroy the crystal structure. Since the deactivated molecular sieve 3A does not easily adsorb water vapor gas but has physical properties similar to those of the molecular sieve 3A provided on the detecting thermosensitive resistance element 2, the deactivated molecular sieve 3A has equivalent thermal properties and substantially an equal thermal capacity, and thus high temperature compensation can be expected.

As illustrated in FIG. 7, in a gas detection device 10, a power supply (voltage source) E is connected to the gas sensor 1 to form a bridge circuit. Specifically, a series circuit of the detecting thermosensitive resistance element 2 and a detecting resistor 11 and a series circuit of the compensating thermosensitive resistance element 2a and a compensating resistor 11a are connected in parallel with respect to the power supply E. Further, output terminals for output voltages Vout1 and Vout2 are respectively connected to a middle of each series circuit so that a differential output therebetween can be detected. Therefore, a minute signal can also be detected.

As illustrated in FIG. 8, the gas detection device 10 includes a microcomputer 12 and a power supply circuit 17 as in the first embodiment, and the circuit illustrated in FIG. 7 is connected to the power supply circuit 17.

The power supply circuit 17 includes the power supply E and controls supply of power to the thermosensitive resistance element 2 by varying the voltage of the power supply E. Specifically, the supply of power by the power supply E in the power supply circuit 17 is controlled by a program stored in storage means of the microcomputer 12. Further, the output voltages Vout1 and Vout2 are input to the microcomputer 12, arithmetically processed, and then output as a detection output.

Further, control of the supply of power of the power supply E is executed by a supply power control unit configured with, for example, the microcomputer 12 and the power supply circuit 17.

Next, an operation of the gas detection device 10 will be described with reference to FIGS. 9 to 11. In the present embodiment, a case of detecting humidity (relative humidity RH) in atmospheric air is described.

As illustrated in FIG. 8, when the gas detection device 10 is driven, a constant voltage of 7 V from the power supply E of the power supply circuit 17 is applied to the detecting thermosensitive resistance element 2 and the compensating thermosensitive resistance element 2a for 30 seconds according to an output signal from the microcomputer 12. This state is a state in which the supply of power is controlled so that the detecting thermosensitive resistance element 2 and the compensating thermosensitive resistance element 2a are heated. Next, a constant voltage of 3 V from the power supply E is applied to the detecting thermosensitive resistance element 2 and the compensating thermosensitive resistance element 2a for 30 seconds. This state is a state in which the supply of power is controlled so that the detecting thermosensitive resistance element 2 and the compensating thermosensitive resistance element 2a are cooled. That is, the detecting thermosensitive resistance element 2 and the compensating thermosensitive resistance element 2a are controlled such that they transition from a heating process to a cooling process. Further, the heating process and the cooling process may be repeated at regular intervals over a plurality of cycles.

A result of change in the output voltages Vout1 and Vout2 in the supply power control as described above are shown in FIG. 9. In FIG. 9, a horizontal axis represents time (seconds) and a vertical axis represents an output voltage (V), and change in the output voltages Vout1 and Vout2 when the humidity is 70% RH are shown. Specifically, a voltage at both ends of the compensating thermosensitive resistance element 2a, a voltage at both ends of the detecting thermosensitive resistance element 2, a voltage at both ends of the compensating resistor 11a in series with the compensating thermosensitive resistance element 2a, and a voltage at both ends of the detecting resistor 11 in series with the detecting thermosensitive resistance element 2 are shown.

As illustrated in FIG. 9, it can be ascertained that a voltage difference is generated between the compensating thermosensitive resistance element 2a side and the detecting thermosensitive resistance element 2 side in a first half of the heating process and cooling process. As illustrated in FIG. 10, this voltage difference increases as water vapor ($H_2O$) is desorbed from the gas molecule adsorption material 3 to cause an endothermic reaction in the heating process, and increases as water vapor ($H_2O$) is adsorbed to the gas molecule adsorption material 3 to cause an exothermic reaction in the cooling process.

In addition, as shown in FIG. 11, a temperature difference is generated between the compensating thermosensitive resistance element 2a and the detecting thermosensitive resistance element 2 to correspond to this voltage difference.

The gas detection device 10 detects humidity in the atmosphere schematically as follows. The output voltages Vout1 and Vout2 are input to the microcomputer 12, arithmetically processed, and then a humidity is detected as a detection output.

When detecting a humidity of, for example 70% RH, in the atmosphere, water vapor ($H_2O$) in the atmosphere is desorbed from and adsorbed to the gas molecule adsorption material 3, the output voltages Vout1 and Vout2 shown in FIGS. 9 to 11 change, and a voltage difference (temperature difference) is generated between the detecting thermosensitive resistance element 2 and the compensating thermosensitive resistance element 2a serving as a reference. On the basis of this voltage difference (temperature difference), the microcomputer 12 calculates and outputs a humidity of 70% RH.

As shown in FIG. 12, it can be ascertained that absolute humidity and the temperature difference are in a proportional relationship. In FIG. 12, a horizontal axis represents absolute humidity ($g/m^3$), and a vertical axis represents a temperature difference (° C.). A correlation between absolute humidity and the temperature difference in an environment of $-10°$ C. is shown, and it can be confirmed that detection of humidity can be effectively performed even under a low temperature environment.

Further, FIG. 13 is a graph in which an influence on gases other than the detection target gas is confirmed, and shows a change in characteristics with respect to ethanol ($C_2H_6O$) as an example. A horizontal axis represents a concentration (%) of ethanol ($C_2H_6O$), and a vertical axis represents a temperature difference (° C.) in a cooling process. It can be ascertained that the temperature difference hardly changes with respect to the concentration of ethanol ($C_2H_6O$), and is not affected even by a high concentration of ethanol ($C_2H_6O$) near an explosion limit. Therefore, a gas detection device with high detection accuracy can be obtained.

In the present embodiment as described above, a heating process (heating step) of heating the gas molecule adsorption material 3 and a cooling process (cooling step) of cooling the gas molecule adsorption material 3 at a temperature lower than that in the heating process are included, and a concentration of a specific gas is detected on the basis of a temperature difference caused by a temperature change (voltage change) of the detecting thermosensitive resistance element 2 and the compensating thermosensitive resistance element 2a.

In the above-described method of detecting a concentration of a gas, a concentration of the gas may be detected from a temperature change in both the heating process and the cooling process, in other words, from a difference in temperature, and a concentration of the gas may be detected from a temperature change in at least one of the heating process and the cooling process, in other words, on the basis of a difference in temperature.

Figure 14:
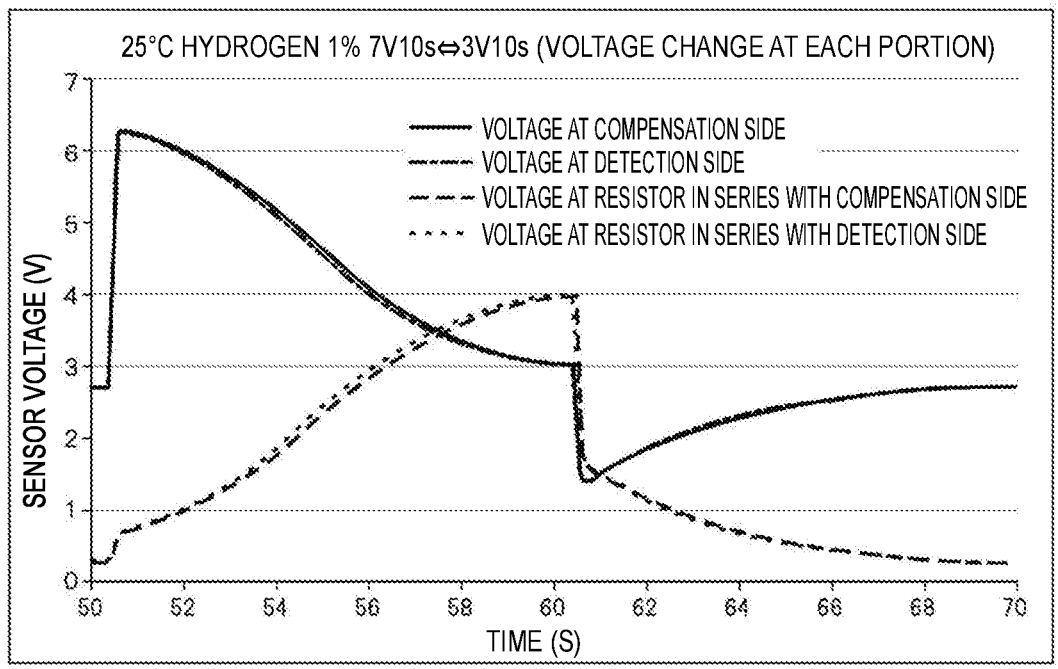
FIG. 14 is a graph showing a third embodiment of the present invention and showing a change in output voltage.
Figure 15:
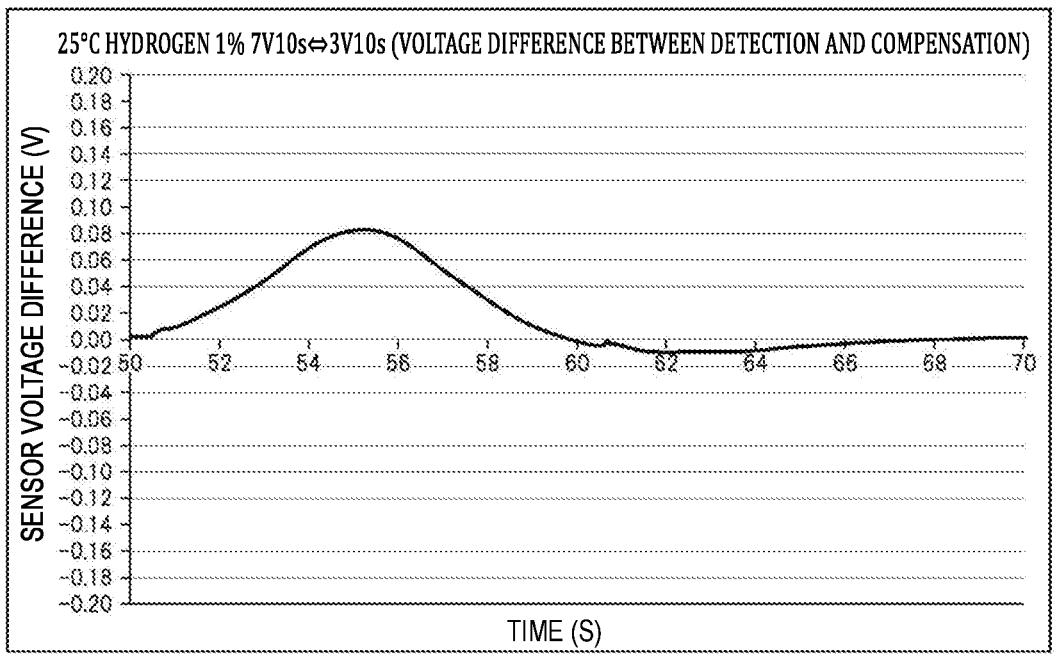
FIG. 15 is a graph showing a voltage difference of the output voltage.
Figure 16:
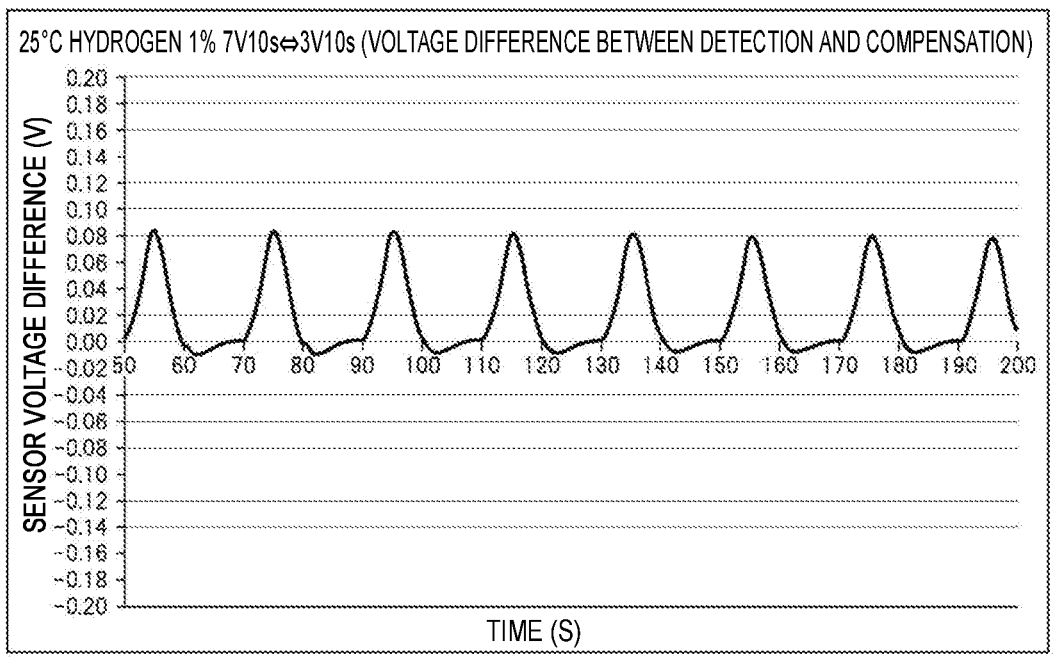
FIG. 16 is a graph showing a voltage difference when a heating process and a cooling process are repeated at regular intervals.
Figure 17:
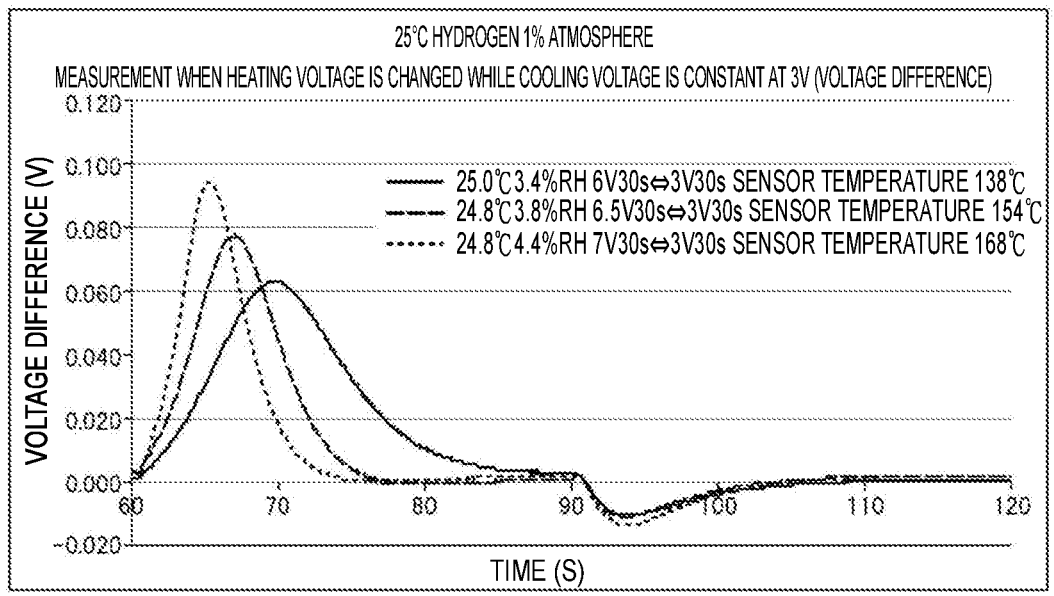
FIG. 17 is a graph showing a voltage difference when a heating temperature is changed.

Next, a third embodiment of the present invention will be described with reference to FIGS. 14 to 17. FIG. 14 shows a change in output voltage, and FIG. 15 is a graph showing a voltage difference between a detecting thermosensitive resistance element and a compensating thermosensitive resistance element. FIG. 16 is a graph showing a voltage difference between the detecting thermosensitive resistance element and the compensating thermosensitive resistance element when a heating process and a cooling process are repeated at regular intervals, and FIG. 17 is a graph showing a voltage difference between the detecting thermosensitive resistance element and the compensating thermosensitive resistance element when a heating temperature is changed in the heating process. The same or corresponding portions as those in the first embodiment and the second embodiment are denoted by the same reference signs, and duplicate description thereof will be omitted.

In the present embodiment, a detection target gas is hydrogen ($H_2$). For example, it is a gas detection device applied to hydrogen stations or fuel cell vehicles in an environment in which a predetermined amount of hydrogen ($H_2$) may be present. The gas detection device has the same configuration as those illustrated in FIGS. 6 to 8 described in the second embodiment. Therefore, a detailed configuration and operation of the gas detection device have been already described, and will be omitted.

As illustrated in FIG. 8, a gas detection device 10 is driven, a constant voltage of 7 V from a power supply E of a power supply circuit 17 is applied to a detecting thermosensitive resistance element 2 and a compensating thermosensitive resistance element 2a for 10 seconds. This state is a heating process. Next, a constant voltage of 3 V from the power supply E is applied to the detecting thermosensitive resistance element 2 and the compensating thermosensitive resistance element 2a for 10 seconds. This state is a cooling process. That is, the detecting thermosensitive resistance element 2 and the compensating thermosensitive resistance element 2a are controlled to transit from the heating process to the cooling process.

Results of changes in output voltages Vout1 and Vout2 in a case of hydrogen ($H_2$) 1% in the supply power control as described above are shown in FIG. 14 (corresponding to FIG. 9).

As illustrated in FIG. 14, it can be ascertained that a voltage difference is generated between the compensating thermosensitive resistance element 2a side and the detecting thermosensitive resistance element 2 side in a first half of the heating process. Further, FIG. 15 shows this voltage difference.

However, in the second embodiment, as illustrated in FIG. 9, in the heating process, water vapor ($H_2O$) is desorbed from the gas molecule adsorption material 3 to cause an endothermic reaction, and the voltage of the detecting thermosensitive resistance element 2 becomes higher than the voltage of the compensating thermosensitive resistance element 2a. In addition, in the cooling process, water vapor ($H_2O$) is adsorbed and an exothermic reaction is generated, and the voltage of the detecting thermosensitive resistance element 2 becomes lower than the voltage of the compensating thermosensitive resistance element 2a.

In contrast, in the present embodiment, as illustrated in FIG. 14, in the heating process, a voltage of the detecting thermosensitive resistance element 2 is lower than a voltage of the compensating thermosensitive resistance element 2a, and in the cooling process, the voltage of the detecting thermosensitive resistance element 2 is slightly higher than the voltage of the compensating thermosensitive resistance element 2a.

That is, when a detection target gas is hydrogen ($H_2$), a correlation opposite to the case of water vapor ($H_2O$) is established. In a case of water vapor ($H_2O$), an endothermic reaction is generated when gas molecules are desorbed from the gas molecule adsorption material 3 in the heating process, and an exothermic reaction is generated when gas molecules are adsorbed to the gas molecule adsorption material 3 in the cooling process. However, in a case of hydrogen ($H_2$), an exothermic reaction is generated when gas molecules are desorbed from the gas molecule adsorption material 3 in the heating process, and a slight endothermic reaction is generated when gas molecules are adsorbed to the gas molecule adsorption material 3 in the cooling process. These characteristics are thought to be attributable to the fact that a boiling point of hydrogen is −259° C. and thus hydrogen can be only in a gaseous state at around room temperature while a state of water molecules is in a liquid state at 0° C. to 100° C.

In addition, using such a difference in characteristics and focusing only on the characteristics of the cooling process, it is possible to detect only water vapor ($H_2O$) even when hydrogen molecules ($H_2$) are present in the atmosphere.

In the gas detection device 10, the output voltages Vout1 and Vout2 are input to the microcomputer 12, arithmetically processed, and then hydrogen ($H_2$) is detected.

When detecting hydrogen ($H_2$) in the atmosphere, hydrogen ($H_2$) is desorbed from and adsorbed to the gas molecule adsorption material 3, the output voltages Vout1 and Vout2 illustrated in FIGS. 14 and 15 are changed, and a voltage difference (temperature difference) is generated between the detecting thermosensitive resistance element 2 and the compensating thermosensitive resistance element 2a that serves as a reference. On the basis of the voltage difference (temperature difference) in the heating process and the cooling process, the microcomputer 12 calculates and outputs a concentration of hydrogen ($H_2$).

When a detection target gas is hydrogen ($H_2$), a voltage difference (temperature difference) is generated mainly due to an exothermic reaction at the time of desorption of gas molecules from the gas molecule adsorption material 3 in the heating process. Therefore, it is possible to detect a concentration of the gas on the basis of at least the temperature change in the heating process, that is, the temperature difference.

As shown in FIG. 16, the heating process and the cooling process may be repeated at regular intervals over a plurality of cycles. Improvement in accuracy of gas detection can be expected by detecting voltage differences of these cycles.

FIG. 17 shows a voltage difference between the detecting thermosensitive resistance element 2 and the compensating thermosensitive resistance element 2a when the heating voltage (temperature) is changed in the heating process. A cooling voltage (temperature) in the cooling process is set to be constant at 3 V and is applied for 30 seconds. A heating voltage is changed to 6 V, 6.5 V, and 7 V, and applied for 30 seconds each.

As a result, a temperature of the detecting thermosensitive resistance element 2 is 138° C. when the heating voltage is 6 V, 154° C. when the heating voltage is 6.5 V, and 168° C. when the heating voltage is 7 V. The heating temperature and a heating rate are changed when the heating voltage is changed, and for example, when the heating voltage is 7 V, it can be ascertained that a peak voltage of the voltage difference appears early. Furthermore, the output voltage tends to increase as the heating temperature increases. Therefore, in the case of hydrogen ($H_2$), it indicates that sensitivity can be easily increased by increasing the heating temperature.

In this manner, a set value can be determined by changing the heating voltage and obtaining an optimal heating temperature and heating rate (time) for a detection target gas.

Further, when comparing characteristics of hydrogen ($H_2$) and water vapor ($H_2O$) as described above, it can be ascertained that required time to reach a maximum value of the voltage difference varies as shown in FIGS. 15 and 10. In the case of the water vapor ($H_2O$) shown in FIG. 10, a maximum value of the voltage difference is obtained in approximately 7 seconds after the heating voltage of 7 V is applied, whereas in the case of hydrogen ($H_2$) shown in FIG. 15, a maximum value of the voltage difference is obtained in approximately 5 seconds after the heating voltage of 7 V is applied.

This is considered to occur because desorption (adsorption) time varies depending on polarity, molecular sizes, or the like of the target. Among four molecules of hydrogen ($H_2$), helium (He), water vapor ($H_2O$) and ammonia ($NH_3$) in the atmosphere, it is known that adsorption takes about 30 minutes for a relatively large-sized ammonia molecule. Therefore, when the cycle of the heating process and the cooling process is set to 60 seconds or 20 seconds as in the respective embodiments, ammonia molecules can be prevented from being detected.

Such a characteristic is considered to be due to a different movement speed of a gas molecule depending on molecules. When this characteristic is utilized, a specific gas can be selectively detected and selectivity of detection target gases can be enhanced by setting the heating time and the cooling time in the heating process and the cooling process or by setting the heating temperature and the cooling temperature.

For example, information on gas molecules of a detection target can be selectively obtained by changing time of one cycle of the heating process and the cooling process, or time of at least one of the heating process and the cooling process. Further, in regards to the heating temperature in the heating process, it has been ascertained that there is an optimum temperature for realizing high sensitivity. In the case of water vapor ($H_2O$), a preferable heating temperature is 150° C. to 170° C., and an optimum temperature is 160° C. When the heating temperature is more than this, the sensitivity decreases. This is because, in the case of water vapor ($H_2O$), an adsorption ability of zeolite decreases as the temperature rises. This indicates that the optimum temperature varies depending on molecules.

Figure 18A:
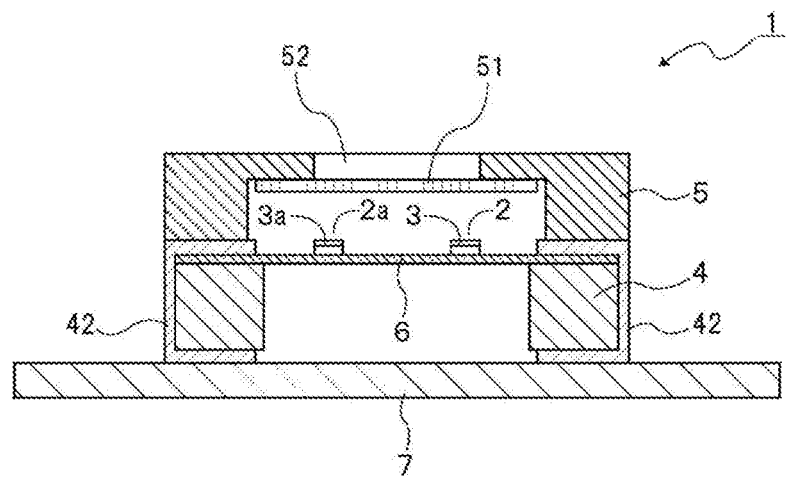
Figure 18B:
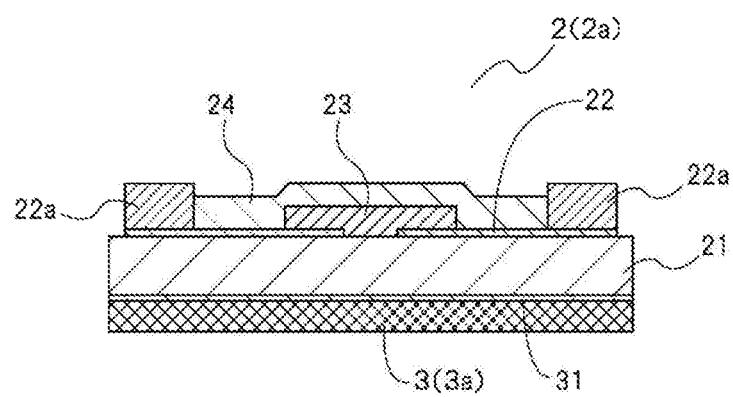
Figure 19:
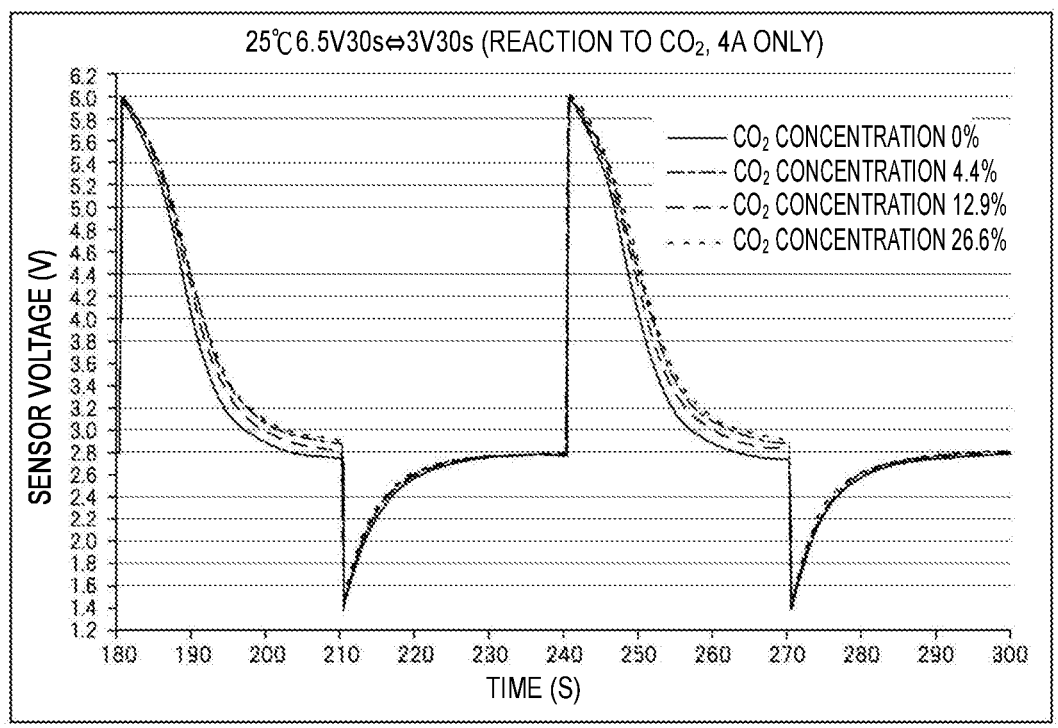
FIG. 19 is a graph showing a change in output voltage.
Figure 20:
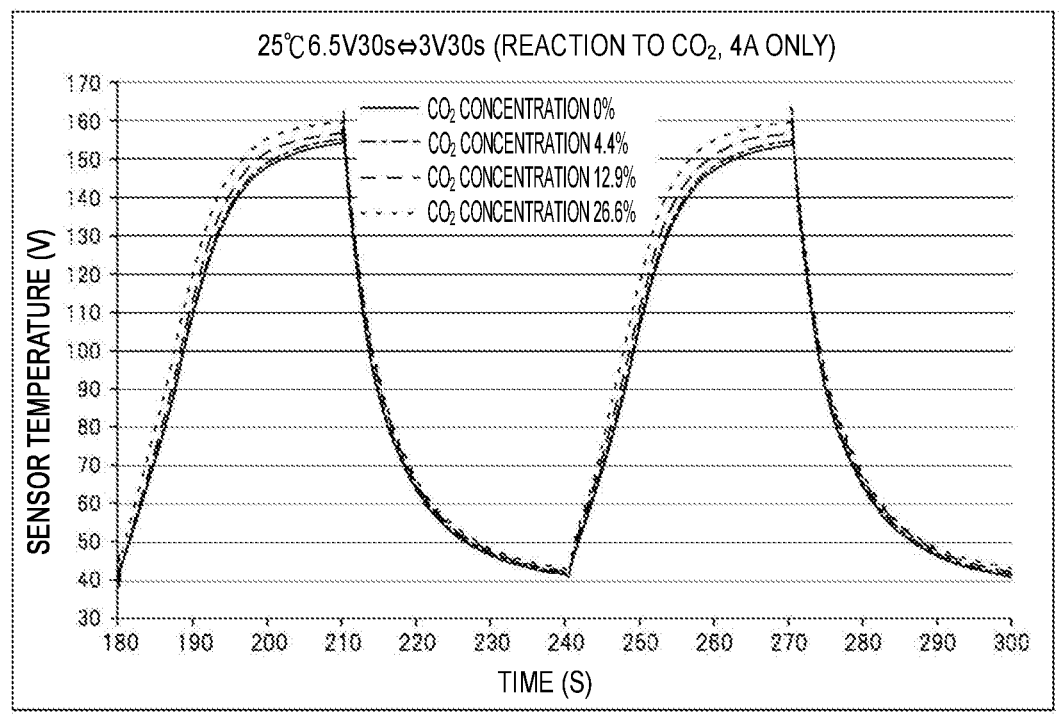
FIG. 20 is a graph showing a change in temperature.

Next, a fourth embodiment of the present invention will be described with reference to FIGS. 18A to 20. FIG. 18A and FIG. 18B are cross-sectional views illustrating a gas sensor, and FIGS. 19 and 20 are graphs showing an output voltage and a temperature change of a detecting thermosensitive resistance element. Portions the same as or corresponding to those in the above-described embodiments are denoted by the same reference signs, and duplicate description thereof will be omitted.

As illustrated in FIG. 18A and FIG. 18B, a gas sensor 1 of the present embodiment is a sensor for detecting carbon dioxide ($CO_2$) in the atmosphere, and is a surface-mount type having a pair of thermosensitive resistance elements. The gas sensor 1 includes a mounting substrate 6, a detecting thermosensitive resistance element 2 and a compensating thermosensitive resistance element 2a disposed on the mounting substrate 6, an exterior case 5 for covering the detecting thermosensitive resistance element 2 and the compensating thermosensitive resistance element 2a, a vent 51, an insulating base member 4, and conductive terminal portions 42 provided on both sides of the base member 4.

The mounting substrate 6 is, for example, a flexible wiring board (FPC) having flexibility. In addition, the conductive terminal portion 42 has a substantially angulated U-shaped cross section, and is a member connecting the detecting thermosensitive resistance element 2 and the compensating thermosensitive resistance element 2a to a wiring pattern formed on a circuit board 7 by electrically connecting a terminal portion formed on the mounting substrate 6 to a terminal portion formed on the circuit board 7.

The detecting thermosensitive resistance element 2 and the compensating thermosensitive resistance element 2a have substantially the same configuration as those described in the first embodiment (see FIG. 1A and FIG. 1B). The detecting thermosensitive resistance element 2 and the compensating thermosensitive resistance element 2a are mounted on the mounting substrate 6 in a facing-down form. In addition, gas molecule adsorption materials 3 and 3a are thermally coupled to and provided for the detecting thermosensitive resistance element 2 and the compensating thermosensitive resistance element 2a respectively. Although the detecting thermosensitive resistance element 2 and the compensating thermosensitive resistance element 2a basically have the same configuration, the gas molecule adsorption material 3 and 3a respectively provided in the detecting thermosensitive resistance element 2 and the compensating thermosensitive resistance element 2a are different in configuration. That is, the porous gas molecule adsorption material 3 provided in the detecting thermosensitive resistance element 2 and the gas molecule adsorption material 3a provided in the compensating thermosensitive resistance element 2a are formed of a material having different adsorption properties.

In the present embodiment, the gas molecule adsorption material 3 provided in the detecting thermosensitive resistance element 2 is a molecular sieve 4A (pore diameter 0.4 nm), and the gas molecule adsorption material 3a provided in the compensating thermosensitive resistance element 2a is a molecular sieve 3A (pore diameter 0.3 nm).

Molecular sieve 4A and molecular sieve 3A have properties of similarly adsorbing hydrogen ($H_2$), helium (He), water vapor ($H_2O$), and ammonia ($NH_3$) in the atmosphere. Therefore, the gas sensor 1 has poor sensitivity to the four gas molecules of hydrogen ($H_2$), helium (He), water vapor ($H_2O$) and ammonia ($NH_3$). On the other hand, other than the four gases described above, the gas sensor 1 has sensitivity to gas molecules that can be adsorbed by the molecular sieve 4A.

Therefore, in the configuration of the gas sensor 1, the sensor is capable of detecting limited gas molecules such as hydrogen sulfide ($H_2S$), carbon dioxide ($CO_2$), ethane ($C_2H_6$), ethanol ($C_2H_6O$), propylene ($C_3H_6$), and butadiene ($C_4H_6$). Among these gas molecules, what is contained in the atmosphere is carbon dioxide ($CO_2$). Therefore, the gas sensor 1 effectively functions as a gas sensor for detecting carbon dioxide ($CO_2$) in the atmosphere.

The gas sensor 1 is connected as illustrated in FIGS. 7 and 8 described in the second embodiment, and is configured similarly as the gas detection device 10. Therefore, since the detailed operation has been already described, description thereof will be omitted.

As illustrated in FIGS. 7 and 8, when the gas detection device 10 is driven, the heating process is executed by applying a constant voltage of 6.5 V of the power supply E of the power supply circuit 17 to the detecting thermosensitive resistance element 2 and the compensating thermosensitive resistance element 2a for 30 seconds, and then the cooling process is executed by applying a constant voltage of 3 V of the power supply E to the detecting thermosensitive resistance element 2 and the compensating thermosensitive resistance element 2a for 30 seconds. Further, the heating process and the cooling process may be repeated at regular intervals over a plurality of cycles.

FIGS. 19 and 20 show an output voltage Vout1 and a temperature change of the detecting thermosensitive resistance element 2, and shows changes when a concentration of carbon dioxide ($CO_2$) is 0%, 4.4%, 12.9%, and 26.6%.

In the present embodiment, as illustrated in FIG. 19, in the heating process, the output voltage Vout1 of the detecting thermosensitive resistance element 2 is lower than a output voltage Vout2 of the compensating thermosensitive resistance element 2a (corresponding to the voltage of the detecting thermosensitive resistance element 2 at a concentration 0%), and in the cooling process, the voltage of the detecting thermosensitive resistance element 2 is slightly higher than the voltage of the compensating thermosensitive resistance element 2a.

That is, when a detection target gas is carbon dioxide ($CO_2$), a correlation opposite to the case of water vapor ($H_2O$) is established as in the case of hydrogen ($H_2$). In the case of carbon dioxide ($CO_2$), an exothermic reaction is generated when gas molecules are desorbed from the gas molecule adsorption material 3 in the heating process, and an extremely slight endothermic reaction is generated when gas molecules are adsorbed to the gas molecule adsorption material 3 in the cooling process. In addition, as shown in FIG. 20, a temperature change occurs in the detecting thermosensitive resistance element 2 to correspond to the change in the output voltage Vout1.

In the gas detection device 10, the output voltages Vout1 and Vout2 are input to a microcomputer 12, arithmetically processed, and a concentration of carbon dioxide ($CO_2$) is detected as a detection output on the basis of the temperature difference.

Next, another embodiment of a gas sensor will be described with reference to FIGS. 21 to 26B. Portions the same as or corresponding to those in the gas sensors of the above-described embodiments are denoted by the same reference signs, and duplicate description thereof will be omitted.

Example 1

Figure 21:
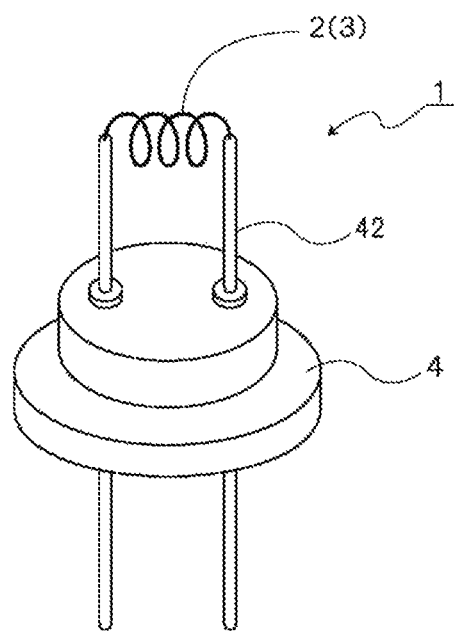
FIG. 21 is a perspective view illustrating another embodiment (Example 1) of a gas sensor of the present invention.

A gas sensor 1 illustrated in FIG. 21 is a prototype gas sensor. A metal wire such as platinum or its alloy wire of 10 µm to 60 µm wound in a coil shape is used for a thermosensitive resistance element 2. In addition, a gas molecule adsorption material 3 is thermally coupled to the thermosensitive resistance element 2. Specifically, the gas molecule adsorption material 3 is applied to surround at least a portion of the thermosensitive resistance element 2 of the metal wire.

In preparing the gas molecule adsorption material 3, for example, after a molecular sieve 3A is finely pulverized using a vibration mill, the finely pulverized powder substances are placed in an electric furnace and heat treated at about 650° C. for 1 hour to remove adsorbed gas molecules. Aluminum hydroxide is added in an amount of 10 wt % to the one from which the adsorbed gas molecules have been removed, which is then further thoroughly pulverized and mixed using a vibration mill, water and glycerin are added thereto, and thereby a slurry of the paste-like gas molecule adsorption material 3 is prepared. On the other hand, both ends of the thermosensitive resistance element 2 of the metal wire are fixed to a conductive terminal portion 42 by spot welding, the gas molecule adsorption material 3 is applied to the thermosensitive resistance element 2 and dried, and then a voltage is applied to the thermosensitive resistance element 2 to cause the thermosensitive resistance element 2 to generate heat and go through heat treatment at about 650° C. for 2 hours. In this manner, the gas molecule adsorption material 3 is provided on the thermosensitive resistance element 2.

Example 2

Figure 22:
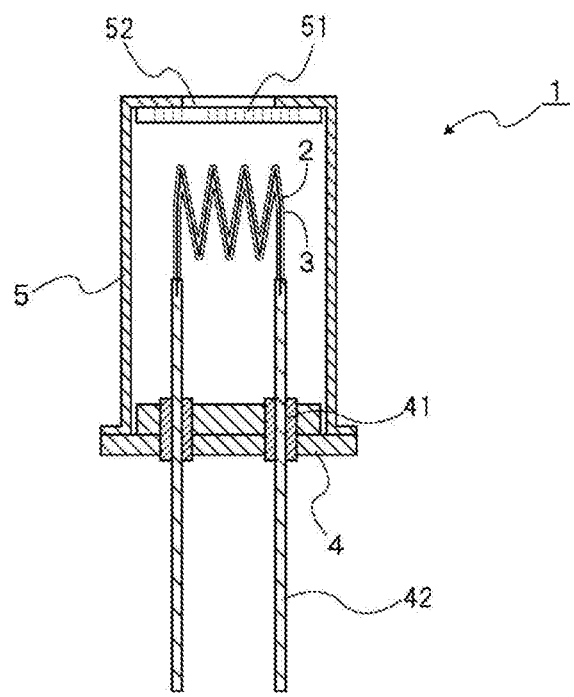
FIG. 22 is a cross-sectional view illustrating the same (Example 2).

A gas sensor 1 illustrated in FIG. 22 basically has the same configuration as the gas sensor described in the first embodiment (see FIG. 1A and FIG. 1B). A difference is that, in the present example, similarly to Example 1, a metal wire such as platinum or its alloy wire of 10 µm to 60 µm wound in a coil shape is used for a thermosensitive resistance element 2. A gas molecule adsorption material 3 is provided on this metal wire.

Example 3

Figure 23:
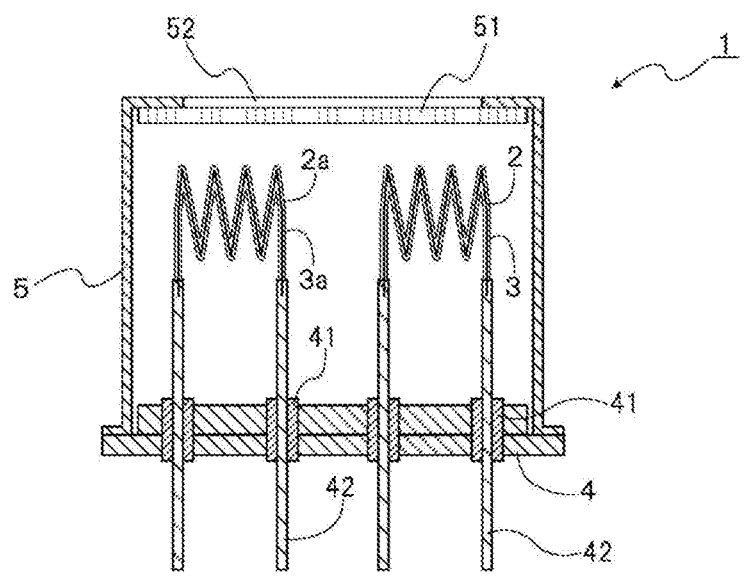
FIG. 23 is a cross-sectional view illustrating the same (Example 3).

A gas sensor 1 illustrated in FIG. 23 basically has the same configuration as the gas sensor described in the second embodiment (see FIG. 6). A difference is that, in the present example, similarly to Example 1, a metal wire such as platinum or its alloy wire of 10 µm to 60 µm wound in a coil shape is used for a detecting thermosensitive resistance element 2, and a gas molecule adsorption material 3 is provided on this metal wire.

On the other hand, similar to the detecting thermosensitive resistance element 2, a metal wire wound in a coil shape is used for a compensating thermosensitive resistance element 2a, but a deactivated molecular sieve 3A of a type A zeolite is used for the gas molecule adsorption material 3a.

The deactivated molecular sieve 3A is prepared by further heat treating the slurry of the paste-like gas molecule adsorption material 3 described in Example 1 at a temperature of about 850° C. for several hours to destroy the crystal structure. This deactivated molecular sieve 3A does not easily adsorb gases. Since the deactivated molecular sieve 3A has physical properties similar to those of the molecular sheave 3A provided on the detecting thermosensitive resistance element 2, the deactivated molecular sieve 3A has equivalent thermal properties and substantially an equal thermal capacity, and thus high temperature compensation can be expected.

Example 4

Figure 24:
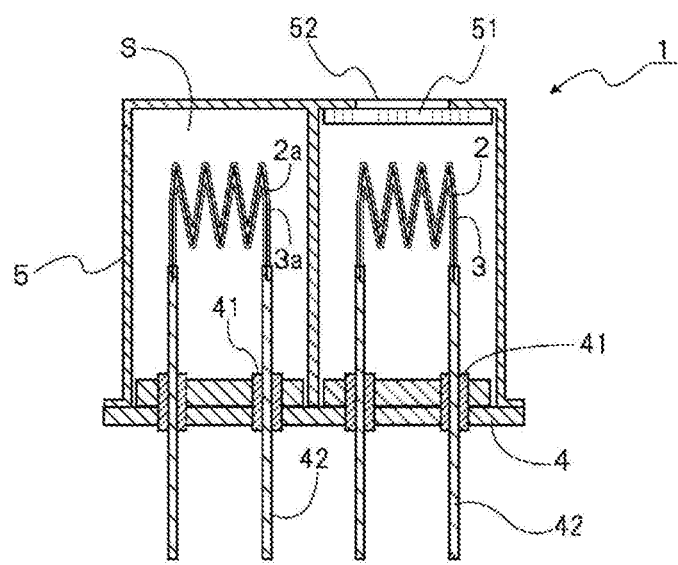
FIG. 24 is a cross-sectional view illustrating the same (Example 4).

A gas sensor 1 illustrated in FIG. 24 is formed such that, in the gas sensor illustrated in Example 3, a side of the compensating thermosensitive resistance element 2a is in a sealed state by an exterior case 5 and the compensating thermosensitive resistance element 2a is accommodated in a sealed space S. Thereby, the detecting thermosensitive resistance element 2 side and the compensating thermosensitive resistance element 2a side can have substantially the same configuration. That is, a gas molecule adsorption material 3a provided on the compensating thermosensitive resistance element 2a can have the same adsorption properties and physical properties as those of a molecule adsorption material 3 provided on the thermosensitive resistance element 2 without being deactivated.

Therefore, the thermosensitive resistance element 2 side and the compensating thermosensitive resistance element 2a side have substantially an equal thermal capacity, and thus high temperature compensation can be realized. Further, the detecting thermosensitive resistance element 2 and the compensating thermosensitive resistance element 2a may use a thin-film thermistor, and are not limited to a particular or specific one.

Example 5

Figure 25:
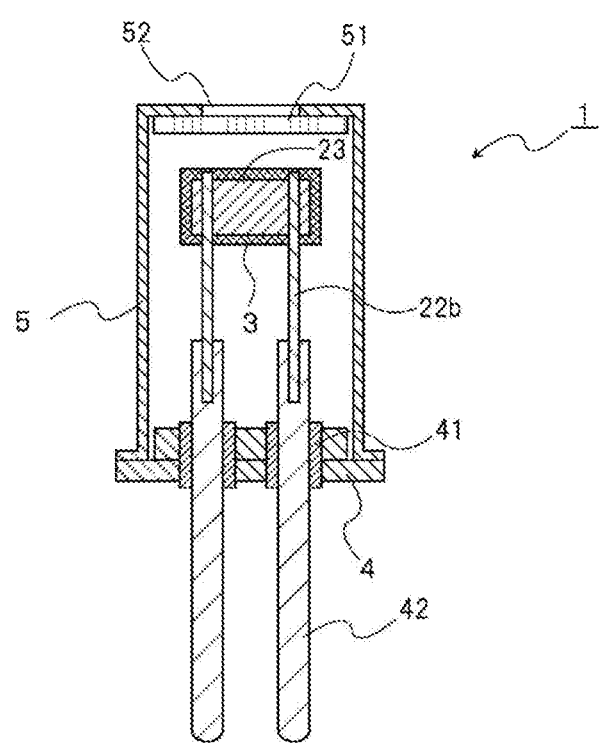
FIG. 25 is a cross-sectional view illustrating the same (Example 5).

A gas sensor 1 illustrated in FIG. 25 basically has the same configuration as the gas sensor described in the first embodiment (see FIG. 1A and FIG. 1B). A configuration of a thermosensitive resistance element 2 is different. The thermosensitive resistance element 2 of the present example is a thermistor element of a type including a thermistor composition 23 and a lead wire 22b of a platinum wire embedded in the thermistor composition 23. The thermistor composition 23 is formed of an oxide thermistor material containing a complex metal oxide as a main component. In addition, the thermistor composition 23 is provided such that a gas molecule adsorption material 3 is applied to surround the thermistor composition 23.

According to the thermosensitive resistance element 2 configured as above, since the thermosensitive resistance element 2 can withstand a high temperature of about 800° C., the gas molecule adsorption material 3 can be provided at the thermistor composition 23 with the same process as the preparation of the gas molecule adsorption material 3 described in Example 1.

Since this sensor can withstand heating at 800° C., when detecting hydrogen ($H_2$), the sensor is a high sensitivity sensor and can detect hydrogen ($H_2$) even at a low concentration of about 1 ppm.

Example 6

Figure 26A:
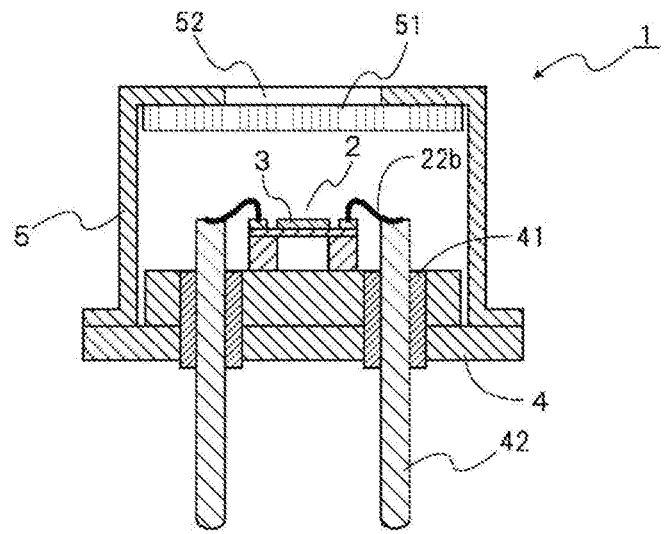
FIG. 26A and FIG. 26B are cross-sectional views illustrating the same (Example 6).
Figure 26B:
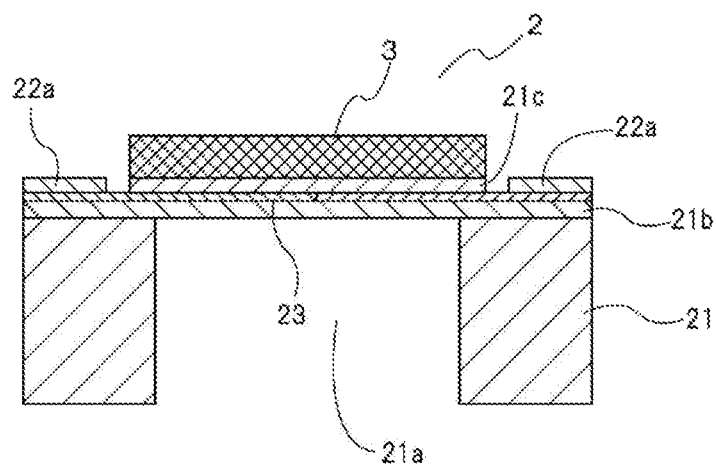

A gas sensor 1 illustrated in FIG. 26A and FIG. 26B is a gas sensor of a micro electro mechanical systems (MEMS) structure. A MEMS chip constituting a thermosensitive resistance element 2 is constituted by a thermopile 23, in which self-heatable thermocouples are connected in series, provided on an insulating film 21b formed on a cavity 21a of a silicon (Si) substrate 21. In addition thereto, the gas molecule adsorption material 3 is provided with the insulating film 21c interposed.

According to the gas sensor 1 having such a MEMS structure, it is possible to realize a sensor with further reduced power consumption and good responsiveness. It is optimal for use in battery-driven gas detectors.

Next, other embodiments of a connection diagram for characteristic detection in gas detection devices will be described with reference to FIGS. 27 to 30. Portions the same as or corresponding to those connection diagrams in the above-described embodiments are denoted by the same reference signs, and duplicate description thereof will be omitted.

Example 1

Figure 27:
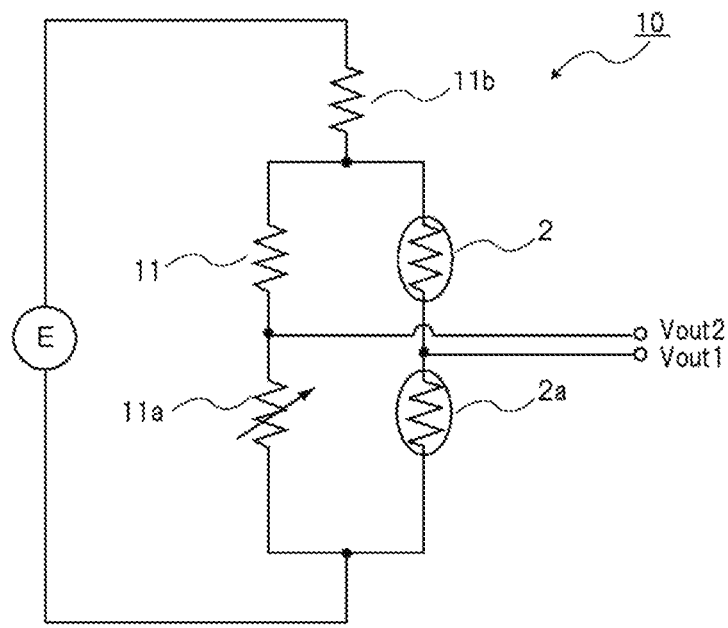
FIG. 27 is a connection diagram illustrating another embodiment (Example 1) for characteristics detection in a gas detection device of the present invention.

As illustrated in FIG. 27, in a gas detection device 10, a power supply (voltage source) E is connected to a gas sensor 1 to form a bridge circuit. A differential output between output voltages Vout1 and Vout2 can be detected, which is the same as the connection diagram illustrated in FIG. 7 of the second embodiment.

A series circuit of a detecting thermosensitive resistance element 2 and a compensating thermosensitive resistance element 2a and a series circuit of a resistor 11 and a variable resistor 11a are connected in parallel with respect to the power supply E via an overcurrent protection resistor 11b.

According to such a configuration, a current having the same current value flows through the detecting thermosensitive resistance element 2 and the compensating thermosensitive resistance element 2a, and thereby an effect of improving temperature compensation can be expected. Further, the variable resistor 11a has a function of adjusting a bridge balance when variations occur in resistance values of the detecting thermosensitive resistance element 2 and the compensating thermosensitive resistance element 2a.

Example 2

Figure 28:
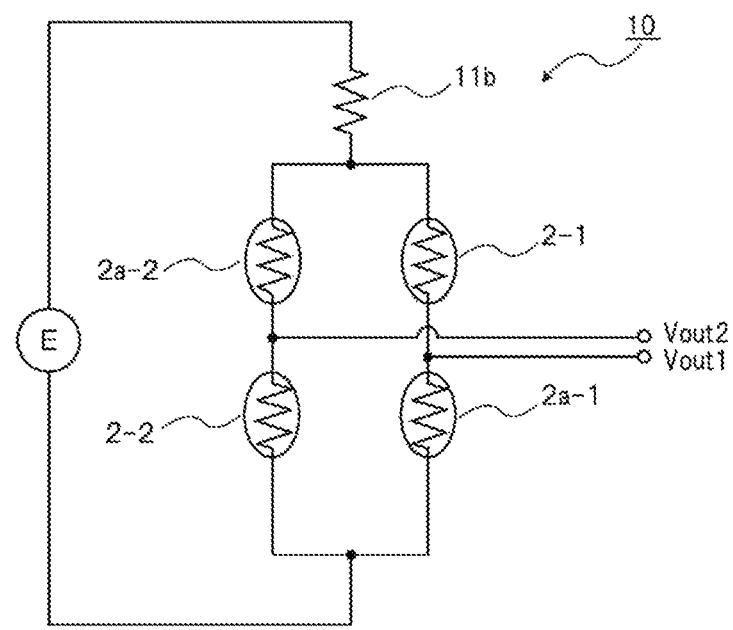
FIG. 28 is a connection diagram illustrating the same (Example 2).

As illustrated in FIG. 28, in a gas detection device 10, a power supply (voltage source) E is connected to a gas sensor 1 to form a full bridge circuit. A differential output between output voltages Vout1 and Vout2 can be detected.

A series circuit of a detecting thermosensitive resistance element 2-1 and a compensating thermosensitive resistance element 2a-1 and a series circuit of a compensating thermosensitive resistance element 2a-2 and a detecting thermosensitive resistance element 2-2 are connected in parallel with respect to the power supply E via an overcurrent protection resistor 11b.

With such a configuration having the full bridge circuit, an output can be doubled, which is effective in detecting a minute amount of gas molecules.

Example 3

Figure 29A:
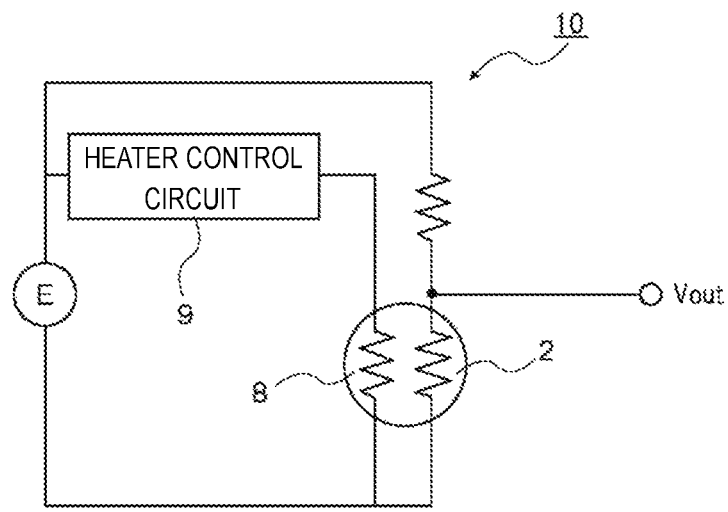

As illustrated in FIG. 29A, a heating element 8 for heating a thermosensitive resistance element 2 and a gas molecule adsorption material 3 is connected to and provided for a gas detection device 10. The heating element 8 is controlled by a heater control circuit 9 so that a heating pattern can be arbitrarily set.

As described above, when the thermosensitive resistance element 2 is self-heated and heat-controlled, a resistance value of the thermosensitive resistance element 2 may change depending on a temperature, which may make the control difficult. In such a case, a heating control can be effectively functioned.

Figure 29B:
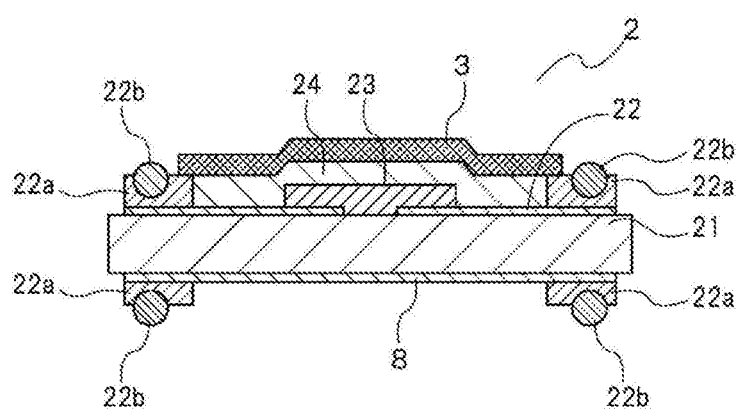

FIG. 29B is a cross-sectional view corresponding to FIG. 1B in the first embodiment. The gas molecule adsorption material 3 is provided on a protective insulating layer 24, and the heating element 8 is provided on a back surface side of a substrate 21.

Example 4

Figure 30:
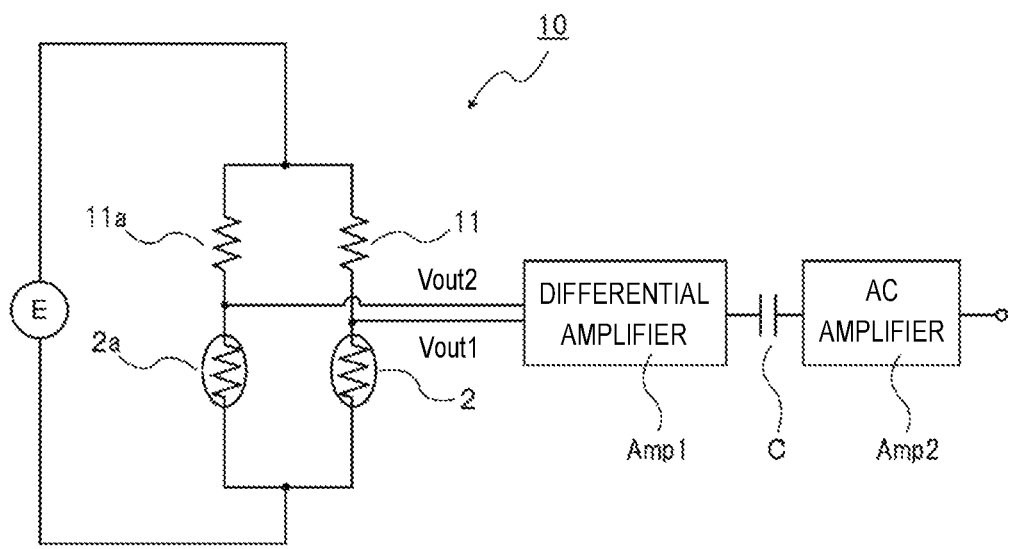
FIG. 30 is a connection diagram illustrating the same (Example 4).

As illustrated in FIG. 30, in a gas detection device 10, an alternating current (AC) power supply (voltage source) E is connected to a gas sensor 1 to form a bridge circuit. A differential output between output voltages Vout1 and Vout2 can be detected. This differential output is connected to a differential amplifier Amp1 and is further connected to an AC amplifier Amp2 via a capacitor C for cutting off a direct current (DC) component, and then is output.

When such an AC amplifier Amp2 is used, since only a signal of a specific frequency can be amplified, immunity to noise can be enhanced, and thus it is effective in detecting a minute amount of gas molecules.

The gas sensor 1 and the connection diagram for characteristic detection described in each of the above embodiments can be arbitrarily combined and applied according to a detection target gas, an application of the gas detection device, or the like.

Further, a porous metal complex can be used for the porous gas molecule adsorption material, Porous metal complexes are a new-concept substance group beyond the boundary between organic compounds and inorganic compounds by utilizing metal complexes. "Coordination polymers (particularly, porous coordination polymers (PCP) having usable nano-sized spaces) or metal-organic framework (MOF)" has attracted attention as new materials.

As described above, according to each of the embodiments, when a heating process in which the porous gas molecule adsorption material is brought into at least a heated state is included, gas molecules are desorbed, and a specific gas can be detected on the basis of the temperature change at that time. As a result, it is possible to improve gas detection sensitivity at low temperature and gas selectivity of detection target gases, and it is possible to reduce power consumption.

Therefore, it is possible to provide a gas sensor, a gas detection device, a gas detection method, and a device provided with a gas detection device having an effect that can improve gas detection performance.

The present invention is not limited to the configurations of the above-described embodiments, and various modifications can be made without departing from the gist of the present invention. In addition, the above-described embodiments have been presented as exemplary and are not intended to limit the scope of the invention. These novel embodiments can be implemented in many other different forms, and various omissions, substitutions, and modifications can be made. The embodiments and modifications thereof should be regarded as being included within the scope and spirit of the invention and included in the invention described in the claims and an equivalent scope thereof.

The invention claimed is:

1. A gas sensor comprising:
a thermosensitive resistance element;
a porous gas molecule adsorption material thermally coupled to the thermosensitive resistance element, wherein the porous gas molecule adsorption material comprises pores having a constant pore diameter, and adsorbs only molecules whose diameter is smaller than the constant pore diameter, and from which a specific adsorbed gas molecule is desorbed by heating; and
a substrate and an adhesive layer, wherein the substrate is interposed between the thermosensitive resistance element and the porous gas molecule adsorption material, and the porous gas molecule adsorption material is held on the substrate through the adhesive layer.

2. The gas sensor according to claim 1, comprising:
a compensating thermosensitive resistance element; and
a material thermally coupled to the compensating thermosensitive resistance element and having adsorption properties different from those of the porous gas molecule adsorption material.

3. The gas sensor according to claim 2, wherein the compensating thermosensitive resistance element is accommodated in a sealed space.

4. The gas sensor according to claim 2, wherein the material having adsorption properties different from those of the porous gas molecule adsorption material is a material in which the porous gas molecule adsorption material is deactivated.

5. The gas sensor according to claim 2, wherein the porous gas molecule adsorption material and the material having adsorption properties different from those of the porous gas molecule adsorption material have equivalent thermal properties.

6. The gas sensor according to claim 1, wherein the thermosensitive resistance element is self-heatable when energized.

7. The gas sensor according to claim 1, wherein a heating element which heats the porous gas molecule adsorption material is provided in addition to the thermosensitive resistance element.

8. The gas sensor according to claim 1, wherein the porous gas molecule adsorption material is a zeolite or a porous metal complex.

9. A gas detection device comprising:
a gas sensor according to claim 1; and
a supply power control unit which controls supply of power to the thermosensitive resistance element and heats the thermosensitive resistance element.

10. The gas detection device according to claim 9, wherein the gas sensor is connected by a bridge circuit and a gas is detected by a differential output thereof.

11. The gas detection device according to claim 10, comprising an alternating current amplifier to which the differential output is connected.

12. A device provided with a gas detection device comprising:
the gas detection device according to claim 9.

13. A gas sensor comprising:
a thermosensitive resistance element;
a porous gas molecule adsorption material thermally coupled to the thermosensitive resistance element, wherein the porous gas molecule adsorption material comprises pores having a constant pore diameter, and adsorbs only molecules whose diameter is smaller than the constant pore diameter, and in which a specific adsorbed gas molecule is desorbed and adsorbed by heating and cooling; and
a substrate and an adhesive layer, wherein the substrate is interposed between the thermosensitive resistance element and the porous gas molecule adsorption material, and the porous gas molecule adsorption material is held on the substrate through the adhesive layer.

14. A gas detection device comprising:
a gas sensor according to claim 13; and
a supply power control unit which controls supply of power to the thermosensitive resistance element, and heats and cools the thermosensitive resistance element.

15. A gas detection method comprising a thermosensitive resistance element, a porous gas molecule adsorption material thermally coupled to the thermosensitive resistance element, a substrate interposed between the thermosensitive resistance element and the porous gas molecule adsorption material, and an adhesive layer holding the porous gas molecule adsorption material on the substrate, wherein the porous gas molecule adsorption material comprises pores having a constant pore diameter, and adsorbs only molecules whose diameter is smaller than the constant pore diameter, and from which a specific adsorbed gas molecule is desorbed by heating, wherein the gas detection method comprises:
a heating step of bringing the porous gas molecule adsorption material into a heated state; and
a detection step of detecting a specific gas using a temperature change of the thermosensitive resistance element due to heating.

16. A gas detection method comprising a thermosensitive resistance element, a porous gas molecule adsorption material thermally coupled to the thermosensitive resistance element, a substrate interposed between the thermosensitive resistance element and the porous gas molecule adsorption material, and an adhesive layer holding the porous gas molecule adsorption material on the substrate, wherein the porous gas molecule adsorption material comprises pores having a constant pore diameter, and adsorbs only molecules whose diameter is smaller than the constant pore diameter, and in which a specific adsorbed gas molecule is desorbed and adsorbed by heating and cooling, wherein the gas detection method comprises:

a heating step of bringing the porous gas molecule adsorption material into a heated state;

a cooling step of bringing the porous gas molecule adsorption material into a cooled state at a temperature lower than that in the heating step; and a detection step of detecting a specific gas using a temperature change of the thermosensitive resistance element due to heating and the cooling.

17. The gas detection method according to claim 16, wherein the heating step and the cooling step are performed by being repeated at regular intervals.

\* \* \* \* \*